US012642479B1

(12) United States Patent
Bibian et al.

(10) Patent No.: US 12,642,479 B1
(45) Date of Patent: *Jun. 2, 2026

(54) SYSTEM FOR TREATING SEIZURES AND ABNORMAL BRAIN FUNCTION

(71) Applicant: NeuroWave Systems Inc., Cleveland, OH (US)

(72) Inventors: Stéphane Bibian, Orange, OH (US); Tatjana Zikov, Orange, OH (US); Mo Modarres, Tampa, FL (US)

(73) Assignee: NeuroWave Systems Inc., Cleveland, OH (US)

( * ) Notice: Subject to any disclaimer, the term of this patent is extended or adjusted under 35 U.S.C. 154(b) by 40 days.

This patent is subject to a terminal disclaimer.

(21) Appl. No.: 18/524,027

(22) Filed: Nov. 30, 2023

Related U.S. Application Data

(63) Continuation of application No. 16/661,154, filed on Oct. 23, 2019, now Pat. No. 11,877,856, which is a continuation of application No. 15/359,733, filed on Nov. 23, 2016, now Pat. No. 10,499,843, which is a continuation of application No. 13/731,315, filed on (Continued)

(51) Int. Cl.
| | |
|---|---|
| *A61B 5/00* | (2006.01) |
| *A61B 5/316* | (2021.01) |
| *A61B 5/369* | (2021.01) |

(52) U.S. Cl.
CPC ............ *A61B 5/4094* (2013.01); *A61B 5/316* (2021.01); *A61B 5/369* (2021.01)

(58) Field of Classification Search
CPC ........ A61B 5/4094; A61B 5/316; A61B 5/369
See application file for complete search history.

(56) References Cited

U.S. PATENT DOCUMENTS

| | | | | | |
|---|---|---|---|---|---|
| 4,417,592 | A | * | 11/1983 | John ...................... | A61B 5/369 346/33 ME |
| 6,246,912 | B1 | * | 6/2001 | Sluijter .............. | A61N 1/36021 607/100 |

(Continued)

OTHER PUBLICATIONS

Huhtala et al., Mining for similarities in aligned time series using wavelets, Aerosense '99, p. 150-160 (Year: 1999).*

*Primary Examiner* — Jacqueline Cheng
*Assistant Examiner* — Tho Q Tran
(74) *Attorney, Agent, or Firm* — Brian Kulkowski

(57) ABSTRACT

The present invention relates to a brain dysfunction and seizure detector monitor and system, and a method of detecting brain dysfunction and/or seizure of a subject. Preferably, the present invention also includes one or more seizure detection algorithms. The analysis method is specifically optimized to amplify abnormal brain activity and minimize normal background activity yielding a seizure index directly related to the current presence of ictal activity in the signal. Additionally, a seizure probability index based on historical values of the aforementioned seizure index, is derived for diagnostic purposes. The seizure probability index quantifies the probability that the patient has exhibited abnormal brain activity since the beginning of the recording. These indexes can be used in the context of emergency and/or clinical situations to assess the status and well-being of a patient's brain, or can be used to automatically administer treatment to stop the seizure before clinical signs appear.

18 Claims, 20 Drawing Sheets

Related U.S. Application Data

Dec. 31, 2012, now Pat. No. 9,538,950, which is a continuation of application No. 12/259,652, filed on Oct. 28, 2008, now Pat. No. 8,538,512, which is a continuation of application No. 12/148,815, filed on Apr. 23, 2008, now Pat. No. 9,554,721.

(60) Provisional application No. 60/925,785, filed on Apr. 23, 2007.

(56) References Cited

U.S. PATENT DOCUMENTS

| | | | | |
|---|---|---|---|---|
| 6,430,437 | B1 * | 8/2002 | Marro | A61B 5/31 |
| | | | | 600/544 |
| 6,658,287 | B1 * | 12/2003 | Litt | A61B 5/4094 |
| | | | | 600/544 |
| 2003/0023183 | A1 * | 1/2003 | Williams | A61B 5/412 |
| | | | | 600/544 |
| 2003/0185408 | A1 * | 10/2003 | Causevic | H03G 3/007 |
| | | | | 381/94.1 |
| 2005/0197590 | A1 * | 9/2005 | Osorio | A61B 5/4094 |
| | | | | 600/544 |
| 2007/0112277 | A1 * | 5/2007 | Fischer | A61B 5/6817 |
| | | | | 600/544 |
| 2007/0149952 | A1 * | 6/2007 | Bland | G16H 50/20 |
| | | | | 604/890.1 |
| 2009/0211346 | A1 * | 8/2009 | Damian | G01N 33/6896 |
| | | | | 73/61.55 |

* cited by examiner

SYSTEM FOR TREATING SEIZURES AND ABNORMAL BRAIN FUNCTION

CROSS-REFERENCE TO RELATED APPLICATION

This application is a continuation of U.S. patent application Ser. No. 16/661,154, which was filed on Oct. 23, 2019, and which is a continuation of U.S. patent application Ser. No. 15/359,733, filed on Nov. 23, 2016 and issued as U.S. Pat. No. 10,499,843 on Dec. 10, 2019, and which is a continuation of U.S. patent application Ser. No. 13/731,315, filed on Dec. 31, 2012 and issued as U.S. Pat. No. 9,538,950 on Jan. 10, 2017, and which is a continuation of U.S. patent application Ser. No. 12/259,652, filed on Oct. 28, 2008 and issued as U.S. Pat. No. 8,538,512 on Sep. 17, 2013, which is a continuation of U.S. patent application Ser. No. 12/148, 815, filed on Apr. 23, 2008 and issued as U.S. Pat. No. 9,554,721 on Jan. 31, 2017, which claims priority from U.S. provisional application No. 60/925,785 filed Apr. 23, 2007. The specifications and drawings of each of the above patents and applications are hereby incorporated by reference in their entirety.

LICENSE RIGHTS-FEDERAL SPONSORED

The U.S. Government has a paid-up license in this invention and the right in limited circumstances to require the patent owner to license others on reasonable terms provided for by the terms of grant number 1 U44 NS057969-01 awarded by the National Institutes of Health and grant number W81XWH-06-C-0016 awarded by Department of Defense USAMRAA.

BACKGROUND OF THE INVENTION

1. Field of the Invention

The present invention relates to a brain dysfunction and seizure detector monitor and system, and a method of detecting brain dysfunction and/or seizure of a subject. The present invention preferably is a system capable of detecting in real time the presence of epileptic activity based on recording of brainwave signal(s) such as scalp electroencephalograms (EEG) or electro-corticograms (ECOG), see FIG. 1. Both signals are used to assess brain function and are the best and most used marker for seizure activity. This system incorporates a state-of-the-art signal processing algorithm based on time-frequency decomposition of the signal, as disclosed herein. This system is intended to be used primarily in the following situations:

- to help first responders such as Emergency Medical Technicians (EMTs) to diagnose the presence of epileptic activity in accident victims or patients for whom no medical information is available,
- to help nursing facilities, intensive care units, emergency rooms, operating rooms etc., to monitor their patients and provide timely treatment, by automatically detecting seizure activity without the need for a trained neurologist or EEG technologist who needs to continuously monitor and interpret EEG recordings,
- to help neurologists and EEG technologists review and mark long term EEG and ECOG recordings for in depth determination of seizure onset, type and location,
- to provide early seizure detection for advanced therapeutics such as Deep-Brain Stimulation and other timely treatment delivery.

2. Technical Background

Detection of seizure activity in EEG and ECOG recordings has been the object of intensive research in the past 50 years. Yet, most of the clinical work in this field still involves offline review of signal tracings by expert EEG technologists trained in the recognition of patterns in the signal indicative of seizure activity.

Seizures are usually classified into convulsive and non-convulsive. Convulsive seizures can be easily observed by attending medical personnel since they involve involuntary muscle movements, convulsion, and twitching. Non-convulsive seizures, on the other hand, are more difficult to diagnose accurately, since the patient is essentially unresponsive with no outward signs of seizure activity, which may be due to a number of factors other than epilepsy. The consequence of seizure activity can be dramatic. Any lasting un-controlled seizure can provoke irremediable brain damage. Timely pharmacological intervention is necessary in order to stop the seizure and lessen the resulting injury. Pharmacological intervention usually involves sedative drugs which essentially suppress cortical activity in order to stop the seizure. This intervention is not without posing risk to the patient, as it also affects the circulatory system (bradychardia, hypotension, etc.). Thus the treatment should be closely supervised by trained medical professionals and it can be particularly risky in patients who already suffer from reduced cardiovascular reserves. It is also particularly risky to administer the treatment to patients whose medical history is not available. Having a means, such as the one disclosed in the present invention, which accurately detects and diagnoses the presence of ictal activity based on electro-physiological recordings can help medical professional in timely decision making to prescribe the adequate treatment. This can be particularly useful in emergency situations, where trained neurologists and EEG technologists may not be available.

Most epileptic patients are aware of their condition and are provided with a prophylactic treatment to control their seizures. They have already been diagnosed and carry with them identification tags which inform first responders of their medical situation in case of emergency. However, there are a number of situations for which a non-epileptic patient may have seizures: traumatic brain injury resulting from a blunt force trauma, concussion, or sudden acceleration/deceleration; poisoning from chemical agents, nerve gas, etc.; high fever. In these cases, seizures may be non-convulsive. First responders who are usually non-EEG experts need to make an accurate determination of the patient state in order to provide timely and adequate treatment. A device such as the one proposed herein answers this need.

Another problem faced by medical teams in emergency situations is drug-seeking individuals faking seizures in order to receive benzodiazepine. These pseudo-seizures are a growing problem in the U.S., where it is estimated that up to 40% of emergency admissions involving patients complaining of seizures are pseudo-seizures who then receive an inadequate treatment instead of the appropriate psychological and counseling help.

In many clinical settings such as geriatric and palliative care, emergency rooms, operating rooms, intensive care units and other hospital settings, patient's life signs are monitored continuously in order to detect medical situations prompting immediate action from attending medical professionals. The presence of seizure, essentially non-convulsive seizures, is often not detected nor diagnosed due to the complexity of having dedicated personnel reviewing streaming EEG or ECoG data in real-time.

An exciting and promising potential treatment to arrest seizures is Deep Brain Stimulation (DBS), where implanted electrodes deliver an electrical shock to the part(s) of the brain where the seizure originates. This electrical shock depletes neuro-transmitters locally, which, in turn, provides an effective barrier that prevents the ictal cascade to proceed beyond its originating point. The deep-brain stimulation treatment relies on the timely detection of the start of the seizure so that it can be applied before the manifestation of clinical signs. This treatment is applied only on a per need basis based on the early detection of the seizure.

Currently available methods of automated EEG analysis for epileptic activity detection have a number of significant disadvantages that prevent their wider utilization in clinical applications, and in particular, emergency and field applications. Such drawbacks include the following: 1) Susceptibility to environmental noise/interference and biological artifacts resulting in poor reliability; 2) Inability to preserve high signal quality resulting in poor reliability; 3) Lack of mobility and portability preventing easy handling, transport and wearability; 4) Lack of robustness and inability to withstand rough handling, water ingress and drop/vibration mechanical shocks; 5) Complex and time consuming application; 6) Complex interpretation of results requiring EEG expert knowledge; 7) Insufficient accuracy; and 8) Delays in detecting abnormal brain activity preventing timely diagnosis and intervention/prevention.

Better systems are needed for many types of applications such as mass casualty; battlefields; mobile hospitals; emergency intervention such as emergency rooms, on ambulances, on airplanes, on ships, and at accident scenes; and locations within a hospital, such as intensive care units and operating rooms. An inexpensive, rugged, and field-deployable means of automatically detecting the presence of EEG seizures and brain dysfunction, followed by rapid and aggressive management, is essential to ameliorate neuropathology from chemical and nerve agent exposure in a mass casualty situation. Accurate detection of a non-convulsive seizure using EEG analysis is of particular importance in treating victims of nerve agent poisoning. A patient could be experiencing status epilepticus (SE), yet due to depleted muscular stores of ATP, the patient will not manifest convulsions. If electrical SE is present, the patient should be given anticonvulsant. However, if no seizure is occurring or the patient is post-ictal, more anticonvulsant could compromise patient respiration and should not be administered. Hence, being able to accurately detect the presence of EEG seizures in such patients is critical for correct treatment.

It is therefore an object of the present invention to provide a system, monitor and method that meets all of the above needs. It is another object of the present invention that this method be inexpensive and/or rapid to conduct. It is still another object of the present invention that this method be usable by a person with no special medical training. It is still another object of the present invention that a patient's therapeutic treatment be more accurately determined based on the quantitative number or profile derived from the testing of the patient. The object of the present invention also is to alleviate the above limitations by providing a rugged and reliable system for acquisition and analysis of brainwaves obtained through intracranial or scalp electrodes (EEG or ECOG signals). The system is compact, ruggedized, watertight and lightweight, preferably easy to attach to a stretcher, IV pole or patient garment such as a belt. It further comprises means for mechanical shock and vibration protection. Such system also provides advanced hardware for shielding the electronics from harmful environmental noise and interferences, and advanced algorithms for the detection and removal of various artifacts that commonly corrupt neurophysiological signals. In addition, electronic means against cardiac defibrillation therapeutic shocks enhances system usage in emergency situations. Continuous measurements of electrode-skin contact and monitoring of signal quality further enhance the reliability of the acquired brainwaves. All the above means ensure the reliability of the system, which is important for guaranteeing the adoption of the system by non-EEG experts and medics, and thus its widespread use. Moreover, the system utilizes highly accurate algorithms for the timely detection of epileptic and other abnormal brain activities. These algorithms and methods are sensitive to such abnormalities. They are specifically designed such that they amplify abnormal activity, while minimizing normal background activity.

SUMMARY OF THE INVENTION

The present invention relates to a brain dysfunction and seizure detector monitor and system, and a method of detecting brain dysfunction and/or seizure of a subject.

The accurate and real-time detection of abnormal brain activity provides the means for the timely warning of impending seizure, thus enabling the timely delivery of therapeutics to stop or abate seizures. Ultimately, our system provides real-time seizure and brain dysfunction detection, and can be used by either experts (e.g., EEG technologists, neurologists, etc.) and, more importantly, non-experts (e.g., first responders, non-medical volunteers). Its use can benefit many clinical applications, in particular emergency and intensive/critical care medicine, neurology/neurosurgery and operating room applications, nursing home applications, field use in civilian and military applications, victim triage, home use and monitoring, etc.

The present invention overcomes the drawbacks of the prior methods for automated seizure detection. Its preferred embodiment enables the timely detection of abnormal brain activity by utilizing ground-breaking advances in signal processing, ergonomics, and electronics. The superior accuracy of the detection is achieved through the use of a redundant wavelet transform, further enhanced by the subsequent synchronization of the wavelet coefficients in the different frequency bands of decomposition. This method tends to amplify abnormal activity and suppress background "normal" activity. The subsequent integration of the amplified abnormal activity followed by the thresholding and resetting mechanisms yields the timely and accurate detection of brain dysfunction patterns such as seizures.

The various embodiments of the system of the present invention were developed for the brain wave or activity monitoring of a single patient or multiple patients. Preferably, the system is a multi-channel EEG system, however, depending on purpose of use and cost, systems may have as few as 1 channel. Preferably, the system or monitor of the present invention also includes one or more seizure detection algorithms. These seizure detection algorithms preferably will combine several parametric and non-parametric multi-EEG methods, as well as the instantaneous level of consciousness and/or wake-sleep states. Preferably, the system or monitor can also measure muscle activity, EMG, contained in the EEG signal. In addition, the system and related methods can use other sensors that measure physiological signals which directly or indirectly result in or from brain dysfunction, or effect or result from brain activity.

Preferably, the system or monitor is constructed to be rugged, so as to withstand transport, handling and use in emergency scenarios, such as on the battlefield or in a mass casualty situation, or to reliably survive daily use by emergency medical personnel or other first responders. The system or monitor should preferably be splash-proof or water tight, dust-tight, scratch-resistant, and resistant to mechanical shock and vibration.

The system or monitor should preferably be portable and field-deployable to a military theater of operation, the scene of an accident, the home of a patient, or to any clinical setting.

Preferably, the system or monitor should preferably be designed for non-expert use. By this, it is meant that a person should not be required to possess extraordinary or special medical training in order to use the system effectively and reliably. Preferably, the system should therefore preferably be automatic in operation in a number of respects. First, the system should be capable of automatic calibration. Second, the system should preferably have automatic detection of input signal quality; for example, the system should be capable of detecting an imbalance in electrode impedance. Third, the system should preferably be capable of artifact detection and removal, so as to isolate for analysis that part of the signal which conveys meaningful information regarding brain dysfunction and/or seizure. Fourth, the system should preferably include seizure detection in the form of algorithms, the outputs of which results in visual and/or audible feedback capable of informing the user whether a patient is currently seizing and/or the probability of a patient having had a seizure at any time during the period of time that the system was monitoring the patient.

The system should preferably operate in real time. One example of real-time operation is the ability of the system to detect a seizure or brain dysfunction event as it is happening, rather than being limited to analysis that takes place minutes or hours afterward.

The processor or computer, and the methods of the present invention preferably contain software or embedded algorithms or steps that: automatically identify seizures or other brain dysfunction based on the amplified abnormal activity or ictal effects; automatically identifies ictal effects from the signals by comparing those effects with a threshold, automatically identifies seizures or other brain dysfunction by first modifying the signal of a subject's brain wave activity to enhance the ictal activity and reduce the background activity related to normal sleep and awake states of the subject; automatically identifies brain dysfunction or seizures by applying a wavelet algorithm to identify ictal effects; automatically identifies seizures or brain dysfunction by using redundant time-frequency decomposition followed by synchronization of ictal effects; automatically identifies seizures or brain dysfunction by combining two or more known or unknown methods of brain wave analysis to obtain a synergistic recognition method; automatically identifies seizures or brain dysfunction by integrating the output of the wavelet analysis combined with synchronization and further applying appropriate thresholds and resetting mechanisms; combinations thereof; and the like.

Preferably, the system described in this invention also preferably incorporates a number of unique features that improve safety, performance, durability, and reliability. The system should be cardiac defibrillator proof, meaning that its electrical components are capable of withstanding the surge of electrical current associated with the application of a cardiac defibrillator shock to a patient being monitored by the system, and that the system remains operable after sustaining such a surge. The system should have shielded leads so as to reduce as much as possible the effects of external electromagnetic interference on the collection of biopotential signals from the patient being monitored by the system. The system should be auto-calibrating, more preferably capable of compensating for the potential differences in the gains of the input channels to the patient module. The system should be capable of performing a continuous impedance check on its electrode leads to ensure the suitability of monitored signals.

Preferably, the system should preferably be population-normed rather than individual-normed. That is to say, the system should be capable of monitoring a patient and making accurate determinations about the patient's brain dysfunction of seizure status without first establishing a baseline measurement of normal brain activity to be used for comparison against suspected dysfunctional brain activity or seizure collected later.

Optionally, the system or monitor may be calibrated or tested via the utilization of a "virtual patient" device, which outputs pre-recorded digital EEG in analog format and in real time in a manner similar to what would be acquired from an actual patient, possibly with data from patients with known brain dysfunction or brain wave abnormalities. This virtual patient can also output any arbitrary waveforms at amplitudes similar to those of EEG signals. These waveforms may be used for further testing of the amplification system, such as for the determination of the amplifier bandwidth, noise profile, linearity, common mode rejection ratio, or other input requirements.

The following are examples of different embodiments of the present invention. One embodiment of the present invention is a device for detecting seizures or brain dysfunction comprising at least two electrodes each having a signal for detecting brain wave activity; and a patient module comprising at least one electronic component, the at least one electronic component capable of inputting the signals from the at least two electrodes for detecting brain wave activity, amplifying ictal effects from the signals, automatically identifying seizures or other brain dysfunction based on the amplified ictal effects, and outputting a calculated signal related to the identified seizures or other brain dysfunction.

Another embodiment of the present invention is a device for detecting seizures or brain dysfunction comprising at least two electrodes each having a signal for detecting a subject's brain wave activity; and a patient module comprising at least one electronic component, the at least one electronic component capable of inputting the signals from the at least two electrodes for detecting brain wave activity, automatically identifying ictal effects from the signals by comparing with a threshold, the threshold being a predetermined number not based on a test subject's own brain wave activity, and outputting a calculated signal related to the identified seizures or other brain dysfunction.

Still another embodiment of the present invention is a device for detecting seizures or brain dysfunction comprising at least two electrodes each having a signal for detecting a subject's brain wave activity; and a patient module comprising at least one electronic component, the at least one electronic component capable of inputting the signals from the at least two electrodes for detecting brain wave activity, modifying the signal of the subject's brain wave activity to enhance the ictal activity and reduce the background activity related to normal sleep and awake states of the subject; automatically identifying ictal effects from the modified signal, and outputting a calculated signal related to the identified seizures or other brain dysfunction.

Yet another embodiment of the present invention is a device for detecting seizures or brain dysfunction comprising at least two electrodes each having a signal for detecting a subject's brain wave activity; and a patient module comprising at least one electronic component, the at least one electronic component capable of applying a wavelet algorithm to automatically identifying ictal effects from the signals, and outputting a calculated signal related to the identified seizures or other brain dysfunction.

Yet another embodiment of the present invention is a device for detecting seizures or brain dysfunction comprising at least two electrodes each having a signal for detecting a subject's brain wave activity; and a patient module comprising at least one electronic component, the at least one electronic component capable automatically identifying ictal effects from the signals, and outputting a calculated signal related to the identified seizures or other brain dysfunction wherein the device is shielded for cardiac defibrillation or like voltages.

Still yet another embodiment of the present invention is a device for detecting seizures or brain dysfunction comprising at least two electrodes each having a signal for detecting a subject's brain wave activity; and a patient module comprising at least one electronic component, the at least one electronic component capable automatically identifying ictal effects from the signals, performing a continuous impedance check on the at least two electrodes and outputting a calculated signal related to the identified seizures or other brain dysfunction.

Even yet another embodiment of the present invention is a device for detecting seizures or brain dysfunction comprising at least two electrodes each having a signal for detecting a subject's brain wave activity; and a patient module comprising at least one electronic component, the at least one electronic component capable automatic calibration of input channels, inputting the signals for detecting a subject's brain wave activity through the input channels, automatically identifying ictal effects from the signals, and outputting a calculated signal related to the identified seizures or other brain dysfunction.

Yet another embodiment of the present invention is a device for detecting seizures or brain dysfunction comprising at least two electrodes each having a signal for detecting a subject's brain wave activity; and a patient module comprising at least one electronic component, the at least one electronic component capable automatically identifying ictal effects from the signals, and outputting a calculated signal related to the identified seizures or other brain dysfunction wherein the device is potted and the at least one electronic component is selected so as to eliminate microphonic effects so as to essentially eliminate any effects on the electrode or outputted signals.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention, and together with the description serve to explain the principles and operation of the invention.

DETAILED DESCRIPTION OF THE INVENTION

Figure 1:
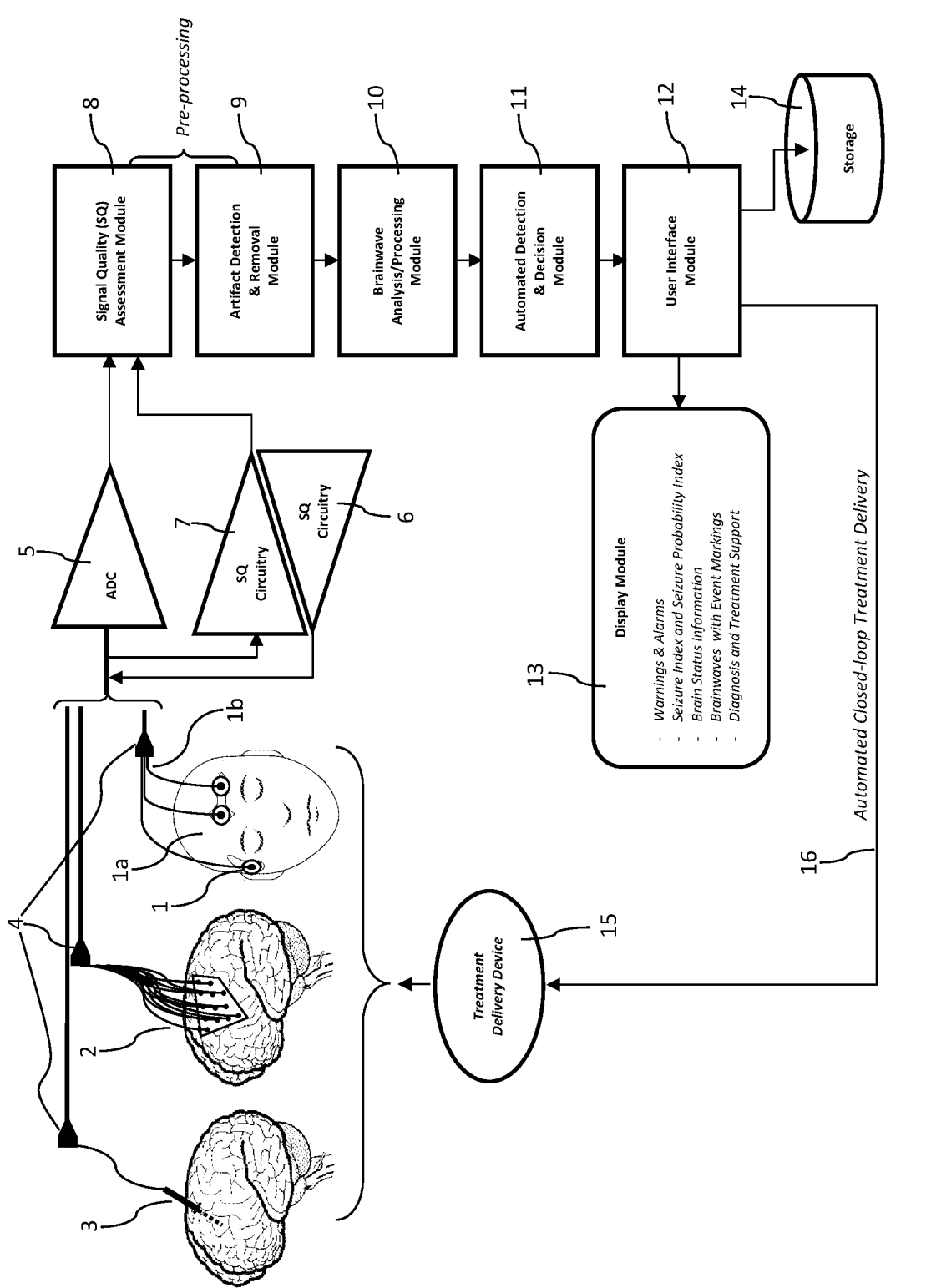
FIG. 1. Block diagram of a system overview for real-time applications.

In the preferred embodiment of the invention, a sensor apparatus comprising, for example, at least two sensor electrodes placed in contact with the skin on the head of a patient, collects at least one channel of brain activity such as an electroencephalogram (EEG) data and transmits the EEG data to a patient module located on or near the patient being monitored. Upon activation by an operator, the patient module initiates an auto-calibration, continuously checks for adequate electrode/skin contact impedance, removes artifacts from the incoming EEG signal, and analyzes the incoming EEG signal using one or more algorithms useful for detecting brain dysfunction or seizure. A visual display on or connected to the patient module and/or one or more audible alarms notify a nearby operator as to the neurophysiological status of the patient, in particular whether or not a patient is currently seizing and the probability of a patient having suffered a seizure at any time in the past while the patient was being monitored by the system. In other embodiments of the invention, the patient module may transmit raw and/or analyzed data to remote locations for data storage, analysis, and/or display, and/or to notify a remote operator of a patient's present or recent neurophysiological status.

Various technologies may be used as part of the sensor suite or apparatus to collect brain activity or related data such as EEG data from the patient. Sensors that are used with various embodiments of the present invention are described herein but can also be any of those known to those skilled in the art for the applications of this invention. These sensors include surface or intracranial electrodes for measuring electrophysiological signals and brain related signals such as EEG, ECOG, EOG, EMG, and the like. These electrophysiological signals or brain related signals can be obtained by any method known in the art, or by any method subsequently developed by those skilled in the art to detect these types of signals.

The sensors can also be magnetic sensors. Since electrophysiological signals are, in general, electrical currents that produce associated magnetic fields, the present invention further anticipates methods of sensing those magnetic fields to acquire brain wave signals similar to those which can be obtained through, for example, an electrode applied to the subject's scalp.

Presently-known and widely-used electrode technologies that may be used by the invention to obtain brainwaves or other brain related-signals such as EEG signals are not limited to, but may include, for example, gold-plated cup electrodes that are filled with conductive paste, pre-gelled electrodes with adhesive backings and snap-on interfaces for the electrode leads, or dry electrodes with penetrators that make contact with the subcutaneous layer of skin.

Typical EEG electrodes connections may have an impedance in the range of from 5 to 10 kiloohms. It is in generally desirable to reduce such impedance levels to below 2 kiloohms. Therefore a conductive paste or gel may be applied to the electrode to create a connection with an impedance below 2 kiloohms. Alternatively or in conjunction with the conductive gel, the subject(s)' skin may be mechanically abraded, the electrode may be amplified or a dry electrode may be used. Dry physiological recording electrodes of the type described in U.S. Pat. No. 7,032,301 are herein incorporated by reference. Dry electrodes provide the advantage that there is no gel to dry out, no skin to abrade or clean, and that the electrode can be applied in hairy areas such as the scalp. Additionally if electrodes are used as the sensor(s), preferably at least two electrodes are used-one signal electrode and one reference electrode; and if further EEG or brain wave signal channels are desired, the number of electrodes required will depend on whether separate reference electrodes or a single reference electrode is used. For the various embodiments of the present invention, preferably an electrode is used and the placement of at least one of the electrodes is on the forehead of the subject's scalp.

The sensor apparatus or suite transmits brainwaves or other brain related signals such as EEG signals to the patient module. In the preferred embodiment of the invention, analog EEG signals are transmitted to the patient module by wires and are digitized and amplified by the patient module, such that the patient is tethered to the patient module during monitoring. Other embodiments may use electrodes or arrays of electrodes that individually amplify and transmit brainwaves or other brain related signals such as EEG signals to a patient module, either wirelessly or through wires, with digitization of the signal taking place either within the electrodes prior to signal transmission or within the patient module following transmission.

In one embodiment of the invention, a harness of electrodes may be used as the sensor apparatus to collect electrophysiological data from a patient. The harness provides the benefit of rapid application for immediate primary monitoring plus optional additional electrode application for more in-depth monitoring as time and situation allow. The electrode harness is composed of two separate parts: a frontal electrodes array, which can be applied in seconds to the forehead of a patient, and a secondary flexible array that covers the entirety of the skull. The frontal array of the electrode harness comprises a strip of electrodes disposed in line on sticky foam tape or similar adhesive surface. Each electrode in the frontal array is connected to a printed circuit that runs along the array and is terminated by a single connector. This connector is used to electrically connect the patient module to the electrode harness. This arrangement is used to acquire two frontal EEG signals and provide a grounding point to the instrumentation amplifiers. Separate electrode connectors can also be used and is preferable.

The secondary flexible array of the electrode harness, which covers the entire skull, may be added if more in-depth monitoring is warranted, or if time and situation allow. This array is preferably made out of stretch material to fit many different head sizes. A single connector may used to connect the flexible array to the frontal array through a secondary mating connector. Jaw straps may be used to maintain the flexible array in place and provide downward mechanical pressure on all electrodes. Besides providing automatic electrode placement, the constant pressure applied by the stretchable fabric of the array ensures continuous skin/ electrode contact, even during patient movement or transport.

In the preferred embodiment of the invention, the electrode leads that transmit signals from the electrodes to the patient module are shielded for improved immunity from electromagnetic interference and resilience to electrostatic discharge. Such electrode lead shielding is standard in electrocardiogram (ECG) devices but is not normally used in EEG devices, as it reduces the input impedance of the amplifier, which then needs to be compensated for by advanced design of the amplifier circuitry. Shielding used in the preferred embodiment of the invention provides the benefit that an operator touching the leads will not create large artifacts in the signal.

The preferred embodiment of the invention includes a patient module comprising electronics in a rugged enclosure, preferably with a visual display and/or an audio speaker and/or a connection to an external display unit with video monitor and/or external speaker, and preferably with one or more ports for connecting the sensor apparatus and/or other equipment, including diagnostic test equipment. The patient module preferably includes a spring-loaded clamp mechanism to provide for its easy mounting on an IV pole, a stretcher, or a hospital bed, and/or a hook hole so that it may be hung on a hook, as from an IV pole. Within the patient module, Brain waves or other brain related signals such as EEG signals are accepted from the sensor apparatus, filtered and processed to arrive at the brain dysfunction or seizure determination reported to the operator via the display and/or audible alarms.

The patient module should preferably be portable, meaning that it should be capable of being moved from one location to another while used or between periods of use while being carried by one or more persons, as defined by International Electrotechnical Commission (IEC) standard 60606-1, sub-clause 2.2.18, the entire standard which is hereby incorporated by reference. Preferably, the patient module weighs less than about 10 pounds. More preferably, the patient module weighs less than about 5 pounds. Even more preferably, the patient module weighs less than about 2 pounds. More preferably still, the patient module weighs less than about 1 pound. Preferably, the patient module is of dimensions less than 7 inches by 4 inches by 2 inches.

The enclosure of the patient module can be constructed from most any rigid material, including, but not limited to, various types of wood, various types of plastics, various types of polymers, various types of resin, various types of ceramics, various types of metals, and various types of composite materials. Preferably the box is constructed of an electrically insulative and lightweight material such as a type of plastic, rigid polymer, fiberglass, carbon fiber composite, or other material with similar characteristics.

The patient module should preferably be of rugged construction, meeting, and preferably exceeding, standards consistent with the requirement for portable equipment to withstand the stresses caused by rough handling and the dangers of ingress by dust or water. Characteristics of rugged equipment include mechanical shock and vibration resistance, scratch resistance on functional and cosmetic surfaces, tightness to dust, and splash proofing or better protection against the ingress of water (preferably water tight enclosure and connectors).

Preferably, the patient module should be resistant to mechanical shock. Mechanical shock resistance is defined by IEC 60601-1, clause 21, the entire reference which is hereby incorporated by reference. Preferably, the enclosure of the patient module should be rigid enough to withstand an inward-directed force of 45 newtons applied over an area of 625 square millimeters anywhere on the surface. Preferably, the enclosure of the patient module should be capable of withstanding blows with an impact energy of 0.5 joules plus or minus 0.05 joules across an area of at most 20 millimeters in diameter by a hammer with Rockwell hardness R100 perpendicular to the surface of the enclosure at any point on the enclosure without breakage of the enclosure or damage to the components enclosed therein. Preferably, the enclosure of the patient module should be capable of surviving a drop of 5 centimeters onto a 50 millimeter thick hardwood board without breakage of the enclosure or damage to the components enclosed therein; more preferably, the patient module should be capable of surviving a drop of 1 meter onto a 50 millimeter thick hardwood board without breakage of the enclosure of damage to the components enclosed therein. Preferably, the carry handles or grips of the patient module should be capable of withstanding a force equal to four times the weight of the patient module without breakage of the patient module enclosure or damage to the components enclosed therein.

Microphonics, the noise introduced into an electronic system undergoing vibration resulting from the physical motion of the electrical components, is detrimental to ambulatory signal acquisition and processing equipment. Signal distortion from microphonic effects may preclude entirely the possibility of acquiring and analyzing useful electrophysiological signals while transporting a patient, for example, during a bumpy ride in a road vehicle such as an ambulance or on a flight in a vibrating aircraft such as a medical helicopter. Therefore, preferably, the patient module should be vibration-resistant, with the objective of maintaining signal integrity while undergoing vibration by reducing microphonic effects. In the preferred embodiment of the invention, shock absorbers are used for the reduction of vibration-induced noise, and adequate potting and discriminate component selection in the construction of the electronics further reduce micro-phonics. Preferably, the patient module should be capable of withstanding vibration at an acceleration spectral density of 0.05 $g^2$ per hertz over the frequency range of 10-500 hertz without breakage of the patient module enclosure or damage to the components enclosed therein.

Preferably, the functional and cosmetic exterior surfaces of the enclosure of the patient module should be resistant to scratches. Scratches or abrasions associated with transport and handling of the patient module should preferably not impair use of the patient module's controls or visual display.

Preferably, the patient module enclosure should be dust-protected, meeting the IEC 50529 IP5X standard for protection against ingress of solid foreign objects, the entire reference which is hereby incorporated by reference. A dust-protected enclosure permits no accumulation of 75 micrometer or smaller diameter particles to a degree or in a location where such accumulation could interfere with the correct operation of the enclosed equipment or impair safety following the test prescribed by the standard. More preferably, the patient module enclosure should be dust-proof, meeting the IEC 50529 IP6X standard for protection against ingress of solid foreign objects, which the reference which is hereby incorporated by reference. A dust-proof permits no observable deposit of 75 micrometer or smaller diameter particles following the test prescribed by the standard.

Preferably, the patient module enclosure should be splash-proof, meeting the IEC 50529 IPX4 standard for protection against ingress of water, the reference which is hereby incorporated by reference. An enclosure is splash-proof if water splashed against the enclosure from any direction does not interfere with the correct operation of the enclosed equipment or impair safety. More preferably, the patient module enclosure should be water-resistant, meeting the IEC 50529 IPX7 standard for protection against ingress of water, the reference which is hereby incorporated by reference. An enclosure is water-resistant if ingress of water in quantities that could interfere with the correct operation of the enclosed equipment or impair safety does not occur when the enclosure is immersed at a depth of 1 meter for 30 minutes. More preferably still, the patient module is water-proof and capable of sustaining indefinite immersion.

EEG equipment used in applications involving patients at risk of cardiovascular failure, and patients under the influence of pharmacological agents causing the depression of the autonomic nervous system, must be designed to be resistant to the shock of a cardiac defibrillator. Therefore, preferably, the patient module of this invention should be cardiac defibrillator-proof, as defined by IEC 60601 Feb. 26, clause 17 h, the entire standard which is hereby incorporated by reference. Without cardiac defibrillator protection, electronic EEG devices can be damaged by the application of a high-voltage cardiac defibrillation shock to a patient to which EEG electrode leads are attached. Preferably, the patient module should be capable of withstanding an electric shock of 5 kilovolts applied directly between any 2 electrodes connected across a 100 ohm resistor load and return to normal operation with 30 seconds after the application of the defibrillation shock without loss of any operator settings or stored data, without damage to the patient module or compromise to the safety of the patient module, and without reducing the energy delivered by the shock to the resistor load by more than 10%. More preferably, the patient module should able to withstand an electric shock of 6 kilovolts applied directly between any 2 electrodes connected across a 100 ohm resistor load and return to normal operation with 5 seconds after the application of the shock without loss of any operator settings or stored data, without damage to the patient module or compromise to the safety of the patient module, and without reducing the energy delivered by the shock to the resistor load by more than 10%. In the preferred embodiment of the invention, cardiac defibrillator proofing is achieved using series resistors in the cable that electrically connects the amplifier to the electrodes. This is standard in electrocardiogram (ECG) devices, but is difficult to implement for EEG devices since it can reduce the common mode rejection ratio and increase the noise profile. As a result, the series resistors must be handpicked to be perfectly balanced. They must also be of a particular technology to reduce the noise.

The patient module can be a separate unit with a signal processor or may be comprised of a data acquisition unit and a base unit with the signal processor in the base unit. Preferably, the patient module comprises at least one electronic component. Also preferably, the signals from one or more of the aforementioned sensors are fed into the connectors on the patient module through the sensor leads. The patient module preferably comprises one or more electrical components which receive these signals, and then wirelessly transmit a signal to a monitor preferably on the patient module. Preferably the patient module has a user interface device to input information or to modify the parameters of the unit, however, in various embodiments this is not necessary.

One optional embodiment of this device is a programmable wireless data acquisition system. This programmable wireless data acquisition system is used to receive the signals from one of more sensors and work with an internal or external processor to analyze the signals. Optionally physiological data may be transmitted between the physiological sensors including electrodes of types described above and the signal processing module using wireless technology. Preferably, the wireless technology is radio frequency based. Most preferably the wireless technology is digital radio frequency based. Preferably, the physiological data is processed to some extend directly in the patient module. More preferably, the physiological data is corrected for artifacts within the patient module, and analyzed for. The physiological signals are transmitted wirelessly to a receiver which can be a base station, a transceiver hooked to a computer, a PDA, a cellular phone, a wireless network, or the like. Most preferably the physiological signals are transmitted wirelessly in digital format to a receiver which can be a base station, a transceiver hooked to a computer, a PDA, a cellular phone, a wireless network, or the like. Wireless signals are both received and transmitted via use of an antenna, preferably external. Frequencies used for transmission are preferably less than about 2.0 GHZ. More preferably, frequencies used for transmission are primarily 902-928 MHz, but Wireless Medical Telemetry Bands (WMTS), 608-614 MHZ, 1395-1400 MHZ, or 1429-1432 MHz can also be used. The present invention may also use other less preferable frequencies above 2.0 GHz for data transmission, including but not limited to such standards as Bluetooth, WiFi, IEEE 802.11, and the like. It is envisioned, but not as preferable that the communication between the patient module and base station or like device can also, or in addition to, be hardwired, instead of wireless. The physiological sensors are generally hard wired to the signal processing unit, but due to the ongoing evolution in wireless sensor technology, signals from physiological sensors will likely be transmitted wirelessly to the signal processing unit, or alternatively, directly to the base station having an integrated signal processing unit, and as such are considered to be part of the present invention. With the advances in MEMS sensor technology the sensors may have integrated analog amplification, integrated A/D converters, and integrated memory cells for calibration; allowing for some signal conditioning directly on the sensor before transmission.

Errors in the form of noise can occur when biopotential data acquisition is performed on a subject. For example, a motion artifact is noise that is introduced to a sensor signal that can result from motion of an electrode that is placed on the skin of a subject. A motion artifact can also be caused by bending of the electrical leads connected to an electrode or even some other sensors. The presence of motion artifacts can result in misdiagnosis, prolong procedure duration and can lead to delayed or inappropriate treatment decisions. Thus, it is imperative to remove motion artifact from the biopotential signal to prevent these problems from occurring during treatment.

For methods of the present invention it is important to reduce motion artifacts from the sensor placement. The most common methods for reducing the effects of motion artifacts in sensors such as electrodes have focused on skin deformation. These methods include removing the upper epidermal layer of the skin by abrasion, puncturing the skin in the vicinity of the electrode, and measuring skin stretch at the electrode site. The methods for skin abrasion ensure good electrical contact between the electrode and the subject's skin. In this method, an abrasive pad is mechanically rotated on the skin to abrade the skin surface before electrode placement. Moreover, medical electrodes have been used with an abrading member to prepare the skin after application of the electrode whereby an applicator gun rotates the abrading member. Methods of skin preparation that abrade the skin with a bundle of fibers have also been disclosed. The methods discussed above provide a light abrasion of the skin to reduce the electrical potential and minimize the impedance of the skin, thereby reducing motion artifacts. However, skin abrasion methods can cause unnecessary subject discomfort, prolong procedure preparation time and can vary based on operator experience. Furthermore, skin abrasions methods can lead to infection, and do not provide an effective solution to long term monitoring. Alternatively dry physiogical recording electrodes could be used, instead of gel electrodes. Dry physiological recording electrodes of the type described in U.S. Pat. No. 7,032,301 are herein incorporated by reference. Dry physiological electrodes do not require any of the skin abrasion techniques mentioned above and are less likely to produce motion artifacts in general.

The above mentioned methods are indeed good practice to follow in the field as they reduce motion artifacts, but they do not completely eliminate motion artifacts. The invention possesses the ability to more completely remove motion and other artifacts by firmware and/or software correction that utilizes information collected preferably from a sensor or device to detect body motion, and more preferably from an accelerometer. These and other artifacts can be denoised by methods such as described in U.S. patent application Ser. No. 10/968,348 to Zikov et al, which is hereby incorporated by reference.

In certain embodiments of the present invention a 3-D accelerometer is directly connected to a microprocessing unit within the micromodule controller. The microprocessing unit receives signal inputs from the accelerometer and a set of Brain waves or other brain related signals such as EEG signals. The microprocessor applies particular tests and algorithms comparing the two signal sets to correct any motion artifacts that have occurred. The processor in one embodiment applies a time synchronization test, which compares the EEG signal data to the accelerometer signal data synchronized in time to detect motion artifacts and then remove those artifacts. Alternatively the processor may apply a more complicated frequency analysis. Frequency analysis preferably in the form of wavelet analysis can be applied to the accelerometer and brainwaves or other brain related signals such as EEG signals to yield artifact detection. Yet another alternative is to create a neural net model to improve artifact detection and rejection. This allows for the system to be taught over time to detect and correct motion artifacts that typically occur during a test study. The above examples are only examples of possible embodiments of the present invention not limitations. The accelerometer data need not be analyzed before wireless transmission, it could be transmitted analyzed by a base station, computer or the like after transmission. As should be obvious to those skilled in the art that a 2-D accelerometer or an appropriate array of accelerometers could also be used. Gyroscopes could be used as well for these purposes.

In addition, a video camera can be used to detect subject movement and position, and the information then used to correct any artifacts that may have arisen from such movement. Preferably the camera is a digital camera. More preferably the camera is a wireless digital camera. Preferably, the video acquired from the camera is then processed so that the subject's movement and position are isolated from other information in the video. The movement and position data that are acquired from the video is then preferably analyzed by software algorithms. This analysis will yield the information needed to make artifact corrections of the physiological signals.

One specific embodiment of the present invention using video subject movement detection involves the use of specially marked electrodes. The electrodes can be any appropriate electrode known in the art. The only change to the electrode is that they preferably have predetermined high contrast marks on them to make them more visible to the video camera. These marking could be manufactured into the electrodes or simply be a sticker that is placed on the back of the electrodes. These markings will make it easier for the video system to distinguish the electrodes from the rest of the video image. Marking each visible electrode will allow for the calculation of the movement of each individual electrode; thus allowing for more accurate artifact correction.

Another specific embodiment of the invention does not require the use of markings on the electrodes; instead the system can detect subject movement from monitoring the actual movement of the subject's body. Software is applied to the video that isolates the position of the subject's body including limbs, then continues to monitor the motion of the subject.

There are numerous advantages to using video over other means of artifact detection and correction. Foremost, video allows for the calculation of movement artifacts from each individual electrode without the need for accelerometers. This makes the use of video very cost effective in relation to other available methods. The video also can be used in conjunction with the accelerometer data to correct for motion artifacts, thus increasing the precision and accuracy of the system's motion artifact correction capabilities.

Various embodiments of the present invention also allow for the flexible use of removable memory to either buffer signal data or store the data for later transmission. Preferably, nonvolatile removable memory can be used as a way to customize the system's buffering capacity and for complete storage of the data. The micro-module controller for the patient module can be programmed to send all signal data to the removable memory or the micro-module controller can be programmed to transmit all data to the base station. If the micro-module controller is programmed to transmit the signal data to the base station wirelessly the removable memory then acts as a buffer. If the patient module loses its wireless connection with the base station, remote communication station or the like, the patient module will temporarily store the data in the removable memory until the connection is restored and data transmission can resume. If however the micro-module controller is programmed to send all signal data to the removable memory for storage then the system does not transmit any information to the base station at that time. That data stored on the removable memory can be retrieved by either wireless transmission from the patient module to the base station or like, or by removing the memory and directly reading. The method of directly reading will depend on the format of the removable memory. Preferably the removable memory is easily removable, that can be removed instantly or almost instantly without tools. In the current embodiment the memory slot is located on the side of the patient module and protected by a plastic cover. The memory is preferably in the form of a card and most preferably in the form of a small easily removable card with an imprint (or upper or lower surface) area of less than about 2 sq. inches. If the removable memory is being used for data storage, preferably it should be of a type that can write data as fast as it is produced by the system, and to possess enough memory capacity for the duration of the test. These demands will obviously depend on the type of test being conducted, tests requiring more sensors, higher sampling rates and longer duration of testing will require faster write speeds and larger data capacity. The type of removable memory used can be almost any type that meets the needs of the test being applied. Some examples of the possible types of memory that could be used include but are not limited to Flash Memory such as CompactFlash, SmartMedia, Miniature Card, SD/MMC, Memory Stick or XD-Picture Card. Alternatively a portable hard drive, CD-RW burner, DVD-RW burner or other data storage peripheral could be used. Preferably, a SD/MMC-flash memory card is used due to its small size. A PCMCIA card is not preferable because of the size and weight.

Preferably, the invention is capable of conducting a RF sweep to detect an occupied frequency or possible interference. The system is capable of operating in two different modes "manual" or "automatic." In the manual mode the system conducts an RF sweep and displays the results of the scan on to the system monitor. The user of the system can then manually choose which frequency or channel to use for data transmission. In automatic mode the system conducts a RF sweep and automatically chooses which frequencies to utilize for data transmission. The system also employs a form of frequency hopping to avoid interference and improve security. The system scans the RF environment then picks a channel to transmit over based on the amount of interference occurring over the frequency range.

Multiple brainwave activity or EEG data acquisition systems or patient modules can be used or are capable of operating simultaneously in the same geographical area without causing interference between the operations of these systems. Preferably two or more subject's can be hooked up to the brain wave activity or EEG data acquisition systems or patient modules of the present invention and operate simultaneously without interference and more preferably through one base station. More preferably at least four subject's can be hooked up to the brain wave activity or EEG data acquisition systems or patient modules of the present invention and operate simultaneously without interference, even more preferably at least six subject's, even more preferably at least eight subject's, still even more preferably at least sixteen subjects, even more preferably at least sixty four subjects, and most preferably at least hundreds of subjects . . .

In various embodiments of the system of the present invention, the system or patient module also can include both a base station, and remote communication station or the like for receiving the transmitted signal from the brainwave activity or EEG data acquisition systems or patient modules. Optionally the base station or patient module may be powered by a Universal Serial Bus (USB) from a computer or similar device, if the base station is a computer or similar device it can be used to power the data acquisition system or patient module. The single USB connection provides the data connection to the computer and the power from the computer to the base station. This allows for quick and simple setup of the base station thereby improving the mobility of the system as a whole. The USB is also beneficial because an additional AC outlet is not needed for the base station. This makes the system when used with a portable laptop, properly equipped PDA or comparable device completely wireless. The USB specification provides a single 5 volt wire from which connected USB devices may power themselves. The bus is specified to deliver up to 500 mA. Because of these power limitations, the base station of the various embodiments of the present invention is unique. This is evidenced by the lack of wireless medical data acquisition systems that employ a base station that is powered solely by a USB connection with the exception of the current invention. It is also evidenced by the much higher power requirements of the other base stations employed by other wireless medical data acquisition systems. Optionally, the patient module can also be powered by batteries.

If a wireless link is used in the system, preferably, the RF link utilizes a two-way (bi-directional) data transmission. By using a two-way data transmission, data safety is significantly increased. By transmitting redundant information in the data emitted by the electrodes, the base station, remote communication station or the like is capable of recognizing errors and request a renewed transmission of the data. In the presence of excessive transmission problems such as, for example transmission over excessively great distances, or due to obstacles absorbing the signals, the base station, remote communication station or the like is capable of controlling the data transmission, or to manipulate on its own the data. With control of data transmission it is also possible to control or re-set the parameters of the system, e.g., changing the transmission channel. This would be applicable for example if the signal transmitted is superimposed by other sources of interference then by changing the channel the remote communication station could secure a flawless and interference free transmission. Another example would be if the signal transmitted is too weak, the remote communication station can transmit a command to increase its transmitting power. Still another example would be the base station, remote communication station or the like to change the data format for the transmission, e.g., in order to increase the redundant information in the data flow. Increased redundancy allows transmission errors to be detected and corrected more easily. In this way, safe data transmissions are possible even with the poorest transmission qualities. This technique opens in a simple way the possibility of reducing the transmission power requirements. This also reduces the energy requirements, thereby providing longer battery life. Another advantage of a two-way, bi-directional digital data transmission lays in the possibility of transmitting test codes in order to filter out external interferences such as, for example, refraction or scatter from the transmission current. In this way, it is possible to reconstruct falsely transmitted data.

The remote communication station can be any device known to receive RF transmissions used by those skilled in the art to receive transmissions of data. The base station, remote communication station or the like by way of example but not limitation can include a communications device for relaying the transmission, a communications device for re-processing the transmission, a communications device for re-processing the transmission then relaying it to another remote communication station, a computer with wireless capabilities, a PDA with wireless capabilities, a processor, a processor with display capabilities, and combinations of these devices. Optionally, the base station, remote communication station or the like can further transmit data both to another device and/or back. Further optionally, two different remote communication stations can be used, one for receiving transmitted data and another for sending data. For example, with the EEG wireless data acquisition system of the present invention, the base station, remote communication system or the like can be a wireless router, which establishes a broadband Internet connection and transmits the physiological signal to a remote Internet site for analysis, preferably by the subject's physician. Another example is where the base station, remote communication system or the like is a PDA, computer or cell phone, which receives the physiological data transmission, optionally re-processes the information, and re-transmits the information via cell towers, land phone lines or cable to a remote site for analysis. Another example is where the base station, remote communication system or the like is a computer or processor, which receives the data transmission and displays the data or records it on some recording medium, which can be displayed remotely or on site for primary caretaker or clinician review and diagnosis, or transferred for diagnosis or analysis at a later time.

The digitized kinetic or physiological signal is then transmitted wirelessly to a base station, remote communication station or the like. This base station, remote communication station or the like allows the subject wide movement. Preferably, the base station, remote communication station or the like can pick up and transmit signals from distances of greater than about 5 feet from the subject, more preferably greater than about 10 feet from the subject, even more preferably greater than about 20 feet from the subject, still even more preferably greater than about 50 feet from the subject, still even more preferably greater than about 200 feet from the subject, and most preferably greater than about 500 feet from the subject. The base station, remote communication station or the like can be used to re-transmit the signal based in part from the physiological signal from the base station, remote communication station or the like wirelessly or via the Internet to another monitor, computer or processor system. This allows the physician or monitoring service to review the subjects physiological signals and if necessary to make a determination, which could include modifying the patients treatment protocols.

Preferably, the patient module should be capable of detecting and filtering high-frequency (HF) interference of the type associated with an electro-surgical unit (ESU). ESUs and other surgical equipment are typical sources of high HF interference at frequencies greater than 100 kHz and amplitudes several orders of magnitude higher than biopotentials like EEG. When such interference creates a slight difference between the noise at the recording electrode site and the noise at the reference electrode site, it may induce the saturation of an instrumentation amplifier collecting electrophysiological signals from a patient. In this case, the acquired signal cannot be salvaged, as it does not contain any viable information. The patient module of the present invention should preferably contain special front-end circuitry to reduce and filter HF interference, for example of the type described in U.S. patent application Ser. No. 11/827,906, hereby incorporated by reference, or similar, thereby providing robustness of brain dysfunction and seizure detection against HF interference. The preferred embodiment of the invention uses a modified Sallen-Key input filter with bootstrap feedback to better guard against harsh interferences, such as those caused by ESUs and electrostatic discharges. The preferred embodiment of the invention also uses a 6 kV isolation interface, which provides a very low leakage capacitance to ground, which in turn furthers the ability of the pre-amplifier to reject disturbances originating from such interferences.

Preferably, the patient module has a low noise characteristic (e.g., less than 1.5 micro volts peak-to-peak for the proper detection of electro-cortical silence-ECS) and wide bandwidth (e.g., preferably 0.125 to 300 Hz to fit a wide population of patients from neonates to the elderly). In addition, preferably at least 1 channel is available, but more preferably 8 channels (the more channels yield the more accurate results) are available. Also, and preferably, automatic calibration procedure during startup is carried out to compensate for the differences in gains of the different channels. More preferably, the patient module has the ability of measuring each electrode impedance at different frequencies (in-band and out-band). This provides 2 advantages: 1) the ability of continuously measuring each electrode impedance for guaranteeing an optimal signal quality; and 2) the ability of detecting whether the electrode is of a good quality (e.g., aged electrodes or poorly shelved electrodes or poor electrolytic gel or wrong electrodes can be detected).

Therefore, the patient module should incorporate the following refinements. First, the patient module should preferably include calibration circuitry for testing the amplifier characteristic. The calibration is systematically carried out during the power-on startup sequence to verify the integrity of the system and its ability to properly acquire Brain waves or other brain related signals such as EEG signals. An automatic calibration during use is preferably provided as well.

An impedance measurement circuitry is preferably added to measure the impedance of each electrode during the initialization sequence. In case of poor electrode impedance, warning messages advise the user to correct the situation (e.g., by repositioning the faulty electrode(s), or re-preparing the electrode site(s)). In addition, preferably the ability of continuously measuring the impedance is provided, without interfering with the EEG frequency band. High electrode impedance is usually cited as the main reason for low signal quality. Having the ability of monitoring the impedance in real time without affecting Brain waves or other brain related signals such as EEG signals improves the robustness of our system as it gives the operator a quantitative measure of signal quality.

Further, a "lead-off" detection circuit is added preferably in case one of the leads gets disconnected. A warning LED on the face plate of the patient module warns the user to check the electrode sensor. To further avoid cross-talk between the disconnected channel and the other operating channels, a relay shorts the inputs of the faulty channel, thereby minimizing its influence on other channels.

Finally, a tribo-electric shielded patient cable is added preferably, which contains cardiac defibrillator resistors and a proprietary circuitry for improving the common mode rejection capability of the system. As compared to standard electrode leads, our cable provided an improvement of over 12 dB in common mode rejection. In addition, the leads have different lengths to easily connect onto a patient, and limit risks for misconnection.

Laboratory test results have confirmed the excellent electrical characteristics of the patient module. In particular, its low noise profile, large bandwidth, excellent common mode rejection and input impedance, surpass the recommendations set by the International Federation of Clinical Neurophysiology (IFCN) for digital EEG recordings. This ensures superior signal quality even in the harshest environments. In addition, clinical tests have revealed that the patient module is immune to severe interferences.

Preferably, the patient module contains a processor or computer unit for analyzing the brain wave and other signals from the electrodes and optionally other signals from the subject. Optionally, the processor or computer unit may also be in a base station or at some remote site. One objective of this invention is to provide a rapid, automated method of brain dysfunction or seizure detection usable by medical personnel not familiar with EEG signal acquisition, analysis, and interpretation.

The real time seizure detector is based on a continuous brainwave signal(s) acquisition coupled with an advanced signal processing method based on redundant joint time-frequency transform such as stationary wavelet transform or, as in preferred embodiment, redundant wavelet packet transform. A preferred embodiment of such method is discussed below. For suboptimal results, other joint time-frequency transforms can be used as well as other frequency domain transforms applied to a short-duration epoch (e.g., short time Fourier transform).

The method preferably of automatic seizure and brain dysfunction detection can be comprised of one or more of 8 distinct steps, which are detailed in the following for a 1-channel system. The steps are:

Step 1: Signal Acquisition and Pre-processing

The system starts by continuously converting the analog brain waves or other brain related signals such as EEG signals into their digital equivalents. The acquired digital EEG epoch contains a defined number of samples in sufficient quantity so that information pertinent to brain function and seizure activity is well represented. In the preferred embodiment, an EEG epoch is 1-second long and digitized at a rate of 128 samples per second. Higher sampling rates can be envisaged in order to obtain a better representation of high frequency activity.

The digital epoch is additionally pre-processed. The pre-processing of the signal is done to remove the 50/60 Hz electromagnetic noise and detect corrupting artifacts. Artifacts can be either physiological (EMG muscle noise, ocular activity, EKG patterns, sweat artifact, etc.) or environmental (noise from lead movement and vibrations, etc.). Epochs heavily corrupted by certain artifacts may not be of sufficient quality to detect seizures. These epochs are thus discarded from the analysis, or, more preferably, de-noised in order to extract the valid EEG or ECoG information embedded in the signal. In the preferred embodiment, wavelet-based de-noising technique, such as described in Zikov et al., U.S. patent application Ser. No. 10/968,348, which is hereby incorporated by reference.

In the preferred embodiment, additional real-time pre-processing functions are used to determine the patient's state of consciousness, the level of muscle activity, the level of ocular activity, the presence of electro-cortical silence (ECS-indicative of potential brain trauma, coma, death, and/or profound pharmacological effect). This information can be used as a complement to or for refinement of the seizure detector detailed below. This information may also be displayed to the user, in addition to the detected seizure activity information, or may be used to trigger specific alarms related to brain status of the patient. This information can also be obtained after the determination of the presence of seizure activity.

The signal quality is first determined by assessing the electrode impedance and measuring the 50/60 Hz content in the original signal. If the signal quality is adequate, the algorithm then proceeds by analyzing the signal for the presence of corrupting artifacts. Whenever possible, these artifacts should be removed from the signal (de-noising function). Artifact-free epochs or de-noised epochs are then analyzed to extract secondary parameters. It then proceeds with the seizure detection outlined in the next Steps.

Step 2: Stationary Wavelet Transform (SWT) and Redundant Wavelet Packet (RWP) Decomposition In the preferred embodiment, a series of digital filters are applied to the analyzed epoch of brain activity. Using a redundant decomposition such as the SWT or RWP allows an enhanced time resolution in comparison to standard (i.e., non-redundant) Wavelet Transform and Wavelet Packet decompositions. The use of redundant transform results in improved accuracy of the epileptic activity detection.

In redundant decompositions, the number of coefficients obtained in each set of coefficients in different frequency bands of decomposition is equal to the number of samples in the analyzed signal epoch. The decomposition is achieved through a filter bank. The filter coefficients of the filter bank at the first level of decomposition are up-sampled at each subsequent level of decomposition in order to obtain the information at that level of decomposition. Conversely to the standard transform, the output of the filter is not down-sampled at each level.

In the preferred embodiment, we use a N=2-level RWP decomposition, where the signal S is decomposed into a $2^N=4$ sets of coefficients corresponding to 4 frequency bands:

$$S \rightarrow \{C_i\}_{i \in [1; 2^N]}, \{C_i\} = \{q_1, q_2, \ldots, q_j, \ldots q_M\}_i \qquad (1)$$

where the coefficients of the set $C_1$ represent the approximation coefficients, the coefficients of the sets $C_2$ to $C_4$ contain the N-level detail coefficients, and where M is the number of samples in each epoch. The decomposition can be performed using any wavelet filter. However, in the preferred embodiment, we use a Daubechies #8 filter, as it captures well the characteristics of typical epileptic patterns such as epileptic spikes. Note that, due to the use of the redundant transform combined with the later synchronization step, it is not necessary to use a wavelet basis function of a low order to achieve good detection of abnormal activity. In fact, the improved recognition is achieved if a higher order wavelet filter is used due to a better frequency separation of the various brain patterns (e.g., artifacts vs. epileptic activity).

Step 3: Synchronization of the RWP Coefficients

Figure 7:
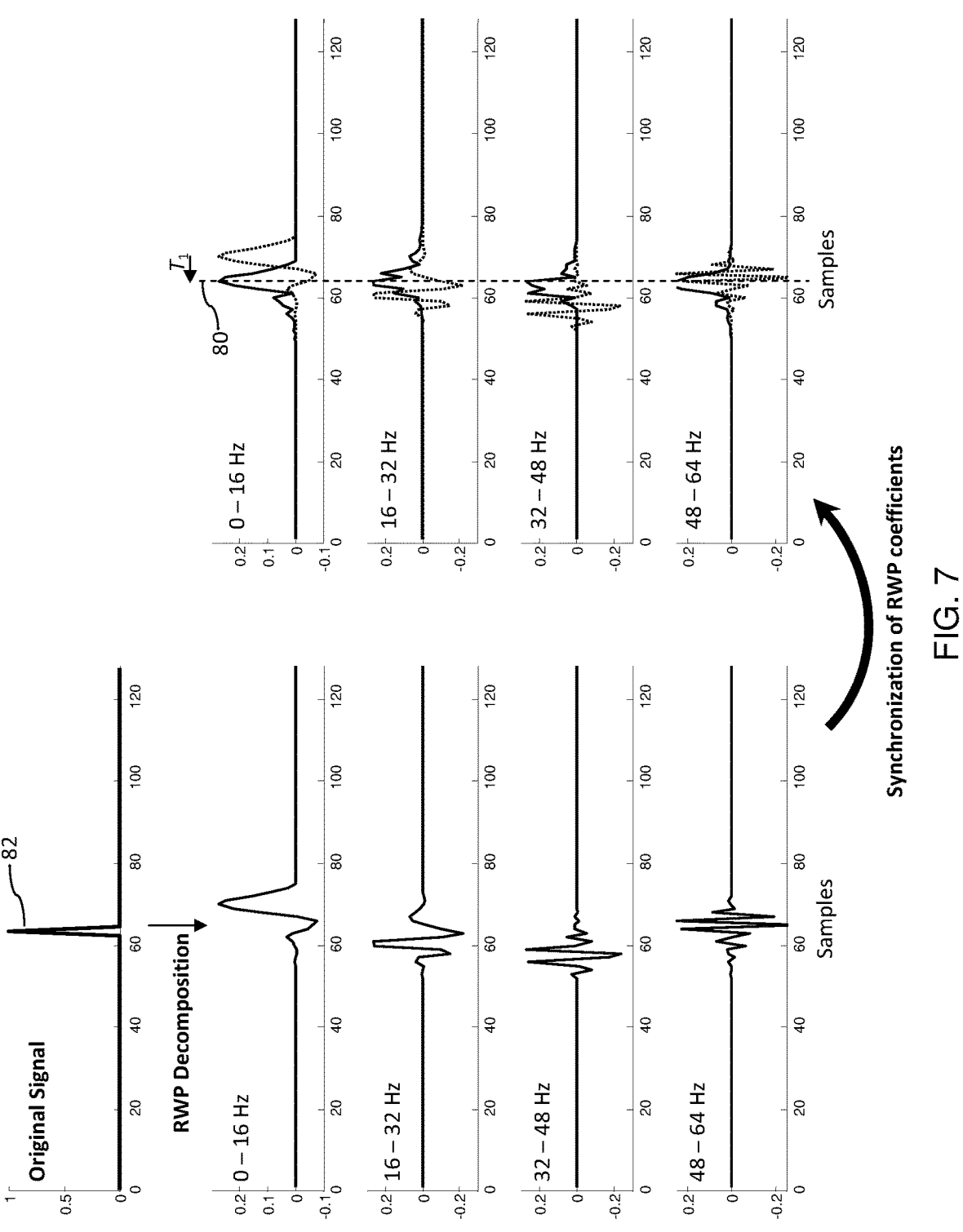
FIG. 7 Examples of synchronization 80 of the RWP coefficients for a single spike.

Due to the nature of the FIR filters used in the decomposition filter banks, time synchrony is of essence. For instance, if a spike is decomposed, such as shown in FIG. 7 later in the application, the coefficients can be observed in the different sub-bands do not peak at the same point in time.

An important principle of the seizure detection method is to detect epileptic spike activity embedded in the signal. In order to improve the detection capability of the algorithm, it is useful to synchronize the wavelet coefficients such that they peak at the same time in each frequency band of decomposition. This is achieved by generating the new coefficient sets $\{Cs_i\}$ defined as:

$$\{Cs_i\} = \qquad (2)$$

$$\{q_1^s, q_2^s, \ldots, q_j^s, \ldots, q_M^s\}_i = \{q_{1-T_i}, q_{2-T_i}, \ldots, q_{j-T_i}, \ldots, q_{M-T_i}\}_i,$$

where $T_i$ is a time shift for the decomposition band i. The time shift depends uniquely on the filter used for the decomposition. It is usually different for each decomposition bands, and can be either positive or negative. Note that whenever $j-T_i < 0$, coefficients obtained from the previous epoch can be used, whereas whenever $j-T_i > M$, the mirror coefficient $M-j+T_i$ can be used instead.

Step 4: Spike Detection

The next step consists of obtaining a set of detection coefficients $D(j)=f(Cs_{i,j})$, where the spike detection function f is a linear or non-linear function optimized for spike detection in Brain waves or other brain related signals such as EEG signals. For example:

$$D(j) = f(Cs_{i,j}) = \prod_{i=1}^{2^N} |C_{i,j-T_i}|. \qquad (3)$$

The function (3) works remarkably well on ECoG signals and signals poorly perturbed by EMG artifacts. For scalp EEG signals, it is often good practice to minimize the weight of the RWP coefficients in higher frequency bands. In the case of N=2-level redundant wavelet packet decomposition based on a signal sampled at 128 S/s, (3) becomes:

$$D(j) = f(Cs_{i,j}) = \prod_{i=1}^{2^N-1} |C_{i,j-T_i}|, \qquad (4)$$

where the coefficients in the 32-64 Hz band were removed from the spike detection function. Likewise, in signals that may be easily perturbed by ocular activity and sweat artifacts, it may be judicious to limit the influence of the low frequency band RWP coefficients. A generalization of (3) is:

$$D(j) = f(Cs_{i,j}) = \prod_{i=1}^{2^N} |(C_{i,j-T_i})|^{\gamma_i}, \gamma_i \in \mathbb{R}, \qquad (5)$$

where the $\gamma_i$ exponents act as weighting factors. Through various optimization procedures, it is possible to define optimal $\gamma_i$ exponents for different EEG and ECoG montages.

Another spike detection function can be based on the sum of the RWP coefficients instead:

$$D(j) = f(Cs_{i,j}) = \sum_{i=1}^{2^N} \alpha_i \cdot |C_{i,j-T_i}|^{\gamma_i}, \; \alpha_i \in \mathbb{R}, \; \gamma_i \in \mathbb{R} \tag{6}$$

where $\alpha_i$ and $\gamma_i$ are weighting factors. Based on a 2-level Daubechies #8 redundant wavelet packet decomposition, we found that the following function works well on scalp EEG data potentially corrupted by EMG artifacts and ocular activity (e.g., fronto-temporal montages):

$$D(j) = |C_1(j+6)| + |C_2(j-3)|^2 + |C_3(j-5)| + |C_4(j+2)| \tag{7}$$

It is further possible for one skilled in the art to define numerous linear or non-linear functions based on this step.

Step 5: Output Filtering

The output of the spike detector is a time series of coefficients with low values during normal brain activity, and very large values during abnormal brain activity such as epileptic spikes. Since seizures are characterized by the rapid succession of such spikes, these large values tend to occur frequently during seizures.

To better characterize periods of seizure and other abnormal brain activity, it may be advantageous to filter the output of the spike detector, which can be done in many different ways.

In one embodiment, the D(j) coefficients are integrated over time. The output of the integrator is reset to 0 whenever the input has been less than a pre-determined threshold H for a pre-determined length of time L. The threshold H can be determined, for example, by analyzing the output of the detector on non-seizure data obtained from healthy subjects or epileptic patients. This data is preferably collected on healthy individuals. The same threshold can be used for each electrode montage, or, preferably, be tuned for each individual channel and different montages. The latency period L should typically be larger than the time between two consecutive spikes during seizures. L can be determined, for example, based on seizure data collected from a population of patients, or based on the current patient data. Similarly to the threshold H, the latency period can be determined for each individual channel and different montages separately.

In the preferred embodiment, the D(j) coefficients are first compared to the threshold H. Whenever D(j)≤H, the coefficient D(j) is set to 0. This effectively removes the background noise associated with normal EEG or ECOG activity from the spike detector coefficients. The de-noised coefficients are then integrated and reset in a similar way as described above. For example, using the spike detector function (6), the noise threshold H can be set to 100 for scalp EEG fronto-temporal montages, and the latency L is about 1 second. It may also be advantageous to limit the amplitude of the spike detector coefficients so that any one coefficient cannot overpower the output of the filter. A secondary threshold H' is then used. Any coefficient D(j) higher than H' is set to the H' value. The secondary threshold may be required for spike detection functions such as (4), which typically yield high values of coefficients. The filtered output of this step is further referred to as $D_o(j)$.

Step 6: Scaling

The output of the output filter in Step #5 is essentially an index of seizure activity. This index can be expressed in an easy to understand scale in order to facilitate its interpretation. In the preferred embodiment, the 0 to 100 scale is used, where a value of 0 is representative of normal brain activity, and a value of 100 is representative of seizure activity. Intermediate values are typically obtained during, for example, the start of seizure activity or isolated spike activity. The resulting index is clamped to 100. Other scales can be envisaged. The resulting scaled seizure index will be referred in the following as the wavelet-based seizure index (WAV$_{SZ}$). The WAV$_{SZ}$ index is computed for every EEG epoch.

Figure 15:
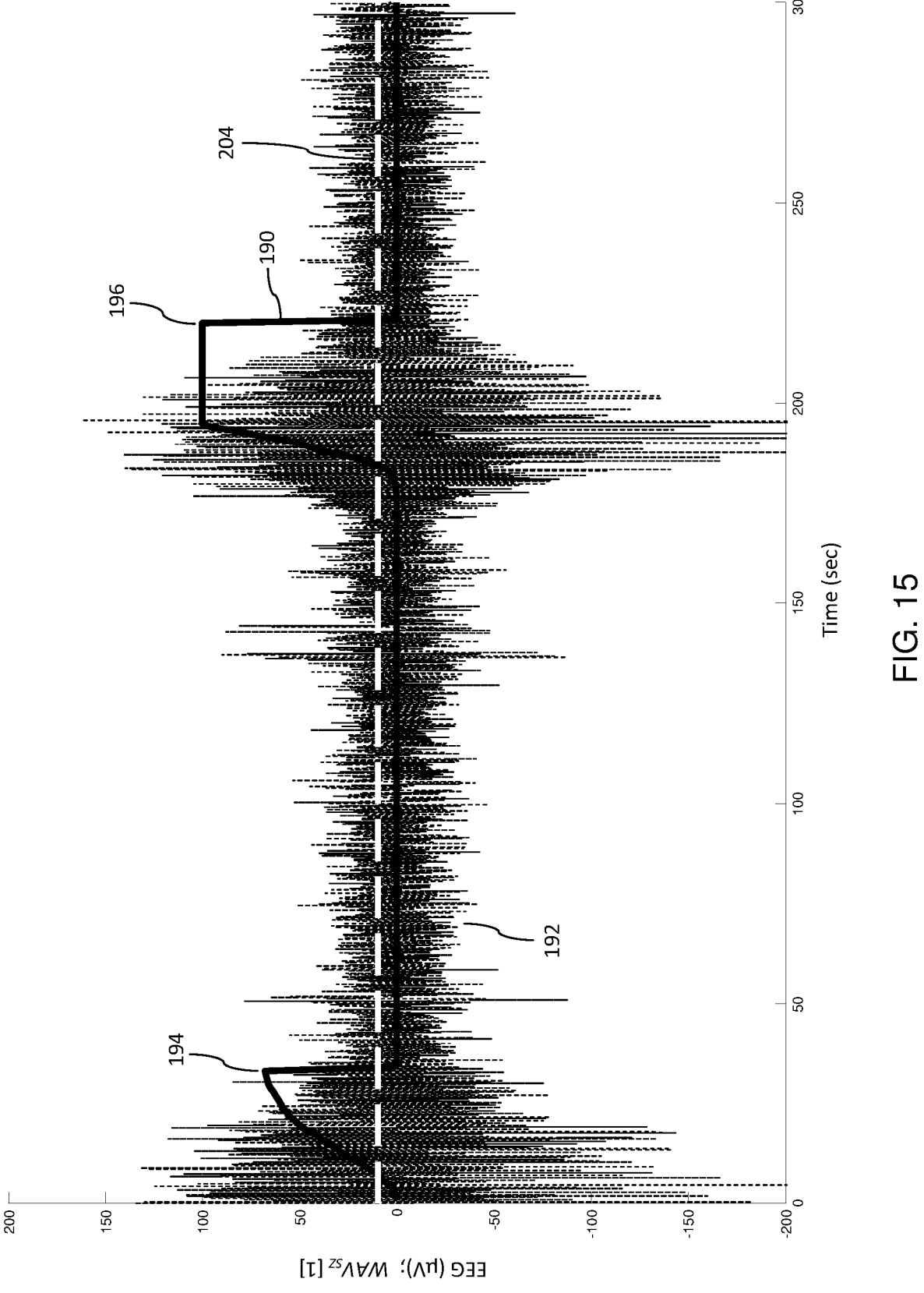
FIG. 15 Example of the $\text{WAV}_{SZ}$ index for a 5-minute scalp EEG recording containing 2 separate generalized seizures.

An example of the WAV$_{SZ}$ index is presented in FIG. 15 shown later in the application for a 5-minute scalp EEG recording containing 2 separate seizures. It is interesting to note how the seizure index resets to 0 immediately upon seizure discontinuation.

Step 7: Go/NoGo Determination

In the preferred embodiment, a seizure threshold $H_s$ between 0 and 100 is applied to the WAV$_{SZ}$ in order to help clinicians and first responders make a Go/NoGo determination related to the presence of seizures. This determination can be done as follow:

$$G(k) = \begin{cases} 1, & iif \; WAV_{sz}(k) > H_S \\ 0, & iif \; WAV_{sz}(k) \le H_S \end{cases} \tag{8}$$

A unique seizure threshold can be applied for all electrode montages. More preferably, the seizure threshold is determined for a specific electrode montage and channels. Montages that are more sensitive to artifacts and muscle movement may have a higher threshold. Montages that are less sensitive to artifact, as well as ECoG recordings may have lower thresholds.

It is important to note that the Go/NoGo seizure detection determination can be made more or less conservative depending on the choice for the seizure threshold. A conservative choice may be judicious in field-like situations, where the presence of corrupting artifacts is typically higher. This effectively reduces the incidence of false positives. Likewise, a low seizure threshold value may be a better choice in controlled clinical environments, or when the patient is unconscious (less EMG and ocular artifacts). In this case, even subtle seizures may be detected by the system.

In the preferred embodiment, the seizure threshold is automatically selected by the system based on statistics involving presence of detected artifacts, signal quality, muscle activity, the patient's consciousness state, or combination thereof. In another embodiment, the seizure threshold is defaulted to an average value. In yet another embodiment, the threshold can be selected by the user of the system.

It is important to note that the Go/NoGo determination has numerous real-time applications, such as automated alarm/warning (visual and auditory), and automated therapeutics administration.

Step 8: Seizure Probability Index

The WAV$_{SZ}$ derived in Step #6, as well as the associated Go/NoGo determination, are representative of the current state of the patient. It is important to note that both the index and the seizure determination reset to their nominal state indicative of normal brain activity as soon as the seizure disappears. In order to provide the system with diagnostic capability, it is then advantageous to add a mechanism through which the patient state can be tracked, i.e., through which the presence of seizure activity in the recent past is accounted for to provide first responders and clinicians with an automated diagnostic tool.

This can be done by computing the probability $P_{SZ}$ that the patient has experienced seizure activity in the recent past. In the preferred embodiment, $P_{SZ}$ is computed as follow:

$$P_{SZ}(k) = \begin{cases} P_{SZ}(k-1) + \dfrac{(WAV_{SZ}(k) \cdot G(k))}{100} - \lambda \\ 0, \; iif \; P_{SZ}(k-1) + \dfrac{(WAV_{SZ}(k) \cdot G(k))}{100} - \lambda < 0 \end{cases}, \quad (9)$$

It is important to note that when $\lambda$=0, the $P_{SZ}$ value increases only when the seizure threshold has been crossed by the $WAV_{SZ}$. While this is rare in the absence of seizures, this may happen when series of non-detected artifacts perturb the recorded signals. These false positives trigger the Go/NoGo determination, which also increases $P_{SZ}$. In order to limit the influence of these false positives, it is therefore important to add a means to reduce $P_{SZ}$ slowly over time. This is achieved through the use of the forgetting factor 2. In the preferred embodiment, where the analysis is performed on a per second basis and the background normal activity is removed from the spike detector coefficients, we can set 2=0.001. It is important to note that this value depends on the sensitivity of the Go/NoGo determination.

The $P_{SZ}$ value is then interpreted in order to provide an appropriate diagnosis. In the preferred embodiment, a simple method consists of having 3 LEDs (green, amber, red). A low $P_{SZ}$ value (between 0 and 0.5) lights only the green LED. An average value (between 0.5 and 20) lights the amber LED. A high value (above 20) lights the red LED. The red LED indicates that the patient most probably suffers seizures. The green LED essentially signifies that the patient had no seizure since the system was attached to the patient and started. The amber LED indicates that further review of the data may be necessary to make an accurate diagnosis.

In another embodiment, the system is provided with a screen and user interface. In this case, text messages and/or pictograms representing the seizure probability index are displayed on the screen.

For real-time operation, Steps #1 thru #8 are repeated often enough to provide a rapid assessment of the patient's state. In the preferred embodiment, a refreshing rate of 1 second is used. Faster refreshing rates can be envisaged. In order to use all of the data, it is preferable that the epoch size be no shorter than the refreshing rate of the algorithm. Having a longer epoch length results in an analysis overlap, which may not be computationally efficient and may be detrimental to real-time implementation.

For this application real time is defined as being less than about 10 minutes, preferably less than about 1 minute, more preferably less than about 20 seconds, even more preferably less than about 5 seconds, still more preferably less than about 1 second, and more preferably less than about 0.1 seconds. Real time can also be based on the minimum unit of time between two samples corresponding to the sampling rate not to be less than 50 Hz.

The previous method was described for operation based on a 1-channel system. Typically, however, multi-channel systems are used in order to observe focal activity, detect focal brain abnormalities, and/or improve the sensitivity and specificity of the analysis.

For a multi-channel system, Steps #1 to #6 are carried through for each individual channel. Additional analyses that are based on the availability of multiple channels (e.g., cross-correlation methods) may be added in Step #1 for a more accurate determination of the patient's brain state. It is also possible to consider that some of the analyses in Step #1 be performed only for a selected subset of channels, thus saving valuable processing resources. For example, consciousness determination and EMG quantification can be done solely on frontal channels. Electro-cortical Silence (ECS) can also be determined based on 1 single channel, as long as the electrode pairs are sufficiently spaced.

Once Steps #1 thru #6 are repeated for each channel, a number of $WAV_{SZ}$ indexes are obtained. These indexes are referred in the following as $$WAV_{SZ}^c,$$

where the superscript c denotes the channel number. The following steps are then applied:
Step #7': Go/NoGo Determination In a multi-channel system, the Go/NoGo determination is done by considering each individual $$WAV_{SZ}^c$$

index. In this case, we expect to see a rise in the $$WAV_{SZ}^c$$

indexes only for the channels where focal seizures are present. A Go/NoGo determination for both focal and generalized seizures is then based on whether the seizure threshold has been crossed by some of the $$WAV_{SZ}^c$$

indexes. In situations involving a limited number of channels, the crossing of the threshold in only one channel may be sufficient to trigger a seizure flag. In this case:

$$G(k) = \begin{cases} 1, & iif \; \max\{WAV_{SZ}^c(k) - H_s^c\}_c > 0 \\ 0, & iif \; \max\{WAV_{SZ}^c(k) - H_s^c\}_c \le 0 \end{cases} \quad (10)$$

where $$H_s^c$$

are channel dependent seizure thresholds. This method gives the highest sensitivity but also the lowest specificity.

As the number of channels increases, such as with a full 10-20 electrode montage, or with a cortical grid, it may be advantageous to trigger the seizure detection only when a pre-defined number of $WAV_{SZ}$ indexes cross their respective seizure thresholds. This effectively reduces the number of false positives, and increases the specificity of the detector.

In yet another embodiment, cluster analysis may be used. In this case, the seizure detection is triggered when a group of closely located electrode pairs acquire signals that contain seizure activity originating from the same source.

Step #8': Seizure Probability Index

The seizure probability index is defined similarly to the 1-channel case, with the difference that the product of the maximum of the $$WAV_{SZ}^c$$

indexes with the Go/NoGo determination of Step #7' is used instead. In the preferred embodiment, where the analysis is done on a per second basis, and where the $$WAV_{SZ}^c$$

indexes are scaled between 0 and 100, the seizure probability index is defined as:

$$P_{SZ}(k) = \begin{cases} P_{SZ}(k-1) + \dfrac{\max\{WAV_{SZ}(k)\}_c \cdot G(k)}{100} - \lambda \\ 0, \; iif \; P_{SZ}(k-1) + \dfrac{\max\{WAV_{SZ}(k)\}_c \cdot G(k)}{100} - \lambda < 0 \end{cases} \quad (11)$$

The brain dysfunction or seizure detection and diagnosis method, which is the object of the present invention, can easily be programmed for real-time applications. Yet, in one embodiment, the method can also be used to analyze pre-recorded data, in order to provide clinicians with an auto-mated review and diagnostic mechanism. In this embodi-ment, the system is composed of a mass storage sub-system which contains the data to be analyzed. The computing means accesses and reads these data, and provides them to the automated seizure detector and diagnosis algorithm. The detector calculates the $$WAV_{SZ}^c$$

indexes and $P_{SZ}$ value based on the provided data. In this embodiment, the computing means downloads the next data epochs as soon as the analysis for the previous epoch has ended. This essentially increases the speed at which the analysis is carried out, and takes full advantage of the processor speed of the computing means.

DETAILED DESCRIPTION OF THE DRAWINGS

Now referring to the FIGS. 1-20, FIG. 1 is a block diagram of a system overview for real-time applications. The system can be connected to the subject either on the subject's scalp 1a with mounted surface electrodes 1, intra-cranial cortical grids 2, or implanted deep brain electrode(s) 3. The electrode leads 1b are preferably connected to the system via a yoke 4 containing cardiac defibrillation resis-tors (not shown) designed to absorb the energy of a cardiac defibrillation pulse. These resistors (not shown) and the associated electronics in the front-end of the instrumentation amplifiers (not shown) are designed to protect the instru-mentation electronic while ensuring that most of the energy delivered by the pulse is used for the intended therapy. The brainwave signals are then amplified and digitized by an Analog-Digital Converter (ADC) circuitry 5.

In addition, a Signal Quality (SQ) circuitry 6, 7 can be used to inject measurement currents into the leads in order to calibrate the instrumentation amplifiers and measure the electrode impedance. A similar SQ circuitry monitors the front-end amplifiers in order to detect eventual saturation that occurs when leads 1b are disconnected. This informa-tion, along with the digitized brainwave signals, is relayed to the processing means 8-14.

The processing means is composed of the sub-systems 8 thru 14. The Signal Quality Assessment Module 8 is used to check whether each signal acquired by the system is of sufficient enough quality to be used in the subsequent analysis. This is done by measuring continuously the elec-trode impedance of each brainwave channel, and by quan-tifying the levels of 50 and 60 Hz noise in the signal. High levels of 50 or 60 Hz indicate either a poor electro-magnetic environment, or a poor connection to the patient which will result in a heightened sensitivity of the system for any other environmental noise (e.g., lead movement, vibration, etc.). High levels of 50 or 60 Hz noise are usually indicative of poor signal quality.

If the signal quality is good, the system proceeds by analyzing the acquired signals in order to detect the presence of environmental or physiological artifacts, which may be corrupting the signal. Some artifacts, such as ocular artifacts, can be removed from the signal by using a de-noising method. This is done at the level of the Artifact Detection & Removal Module 9.

De-noised and artifact-free signals are sent to the Brain-wave Analysis/Processing Module 10. This sub-system derives information contained in the signal, such as the level of consciousness of the patient, the presence of electro-cortical silence, the level of ocular activity, the level of muscle activity (EMG), etc. This information can be used as a complement to the real-time seizure detector to provide a better diagnostic means to the user. Some of this information may also be used in the real-time seizure detector to tune properly the different thresholds used by the underlying algorithm.

The Automated Detection & Decision Module 11 is at the core of the real-time seizure detector. It uses a method that amplifies abnormal spike activity in the signal, while mini-mizing the background "normal" brain activity. It also combines the real-time seizure index with the information obtained in the Brainwave Analysis/Processing Module 10 in order to provide an accurate diagnostic of the patient's brain state.

A User Interface Module 12 provides the means for the user to interact with the system. In the preferred embodi-ment, this is done through the use of a display 13, which can be a touch screen display. The display 13 is used to warn the user, in real-time, of the presence of seizures. In addition, the User Interface Module 12 archives all the acquired signals and processed variables into a mass storage device 14 for later review.

Finally, in some embodiments, the system is connected to mechanism that automatically delivers a treatment to the patient, referred in the schematic as the Treatment Delivery Device 15. The output of the system through a processor (not shown) can be used with the Treatment Delivery Device in closed loop 16 to automatically deliver physical, electrical or chemical treatment to the subject automatically based on the occurrence of abnormal brain activity, and monitor the effectiveness of such treatment in real time.

Figure 2:
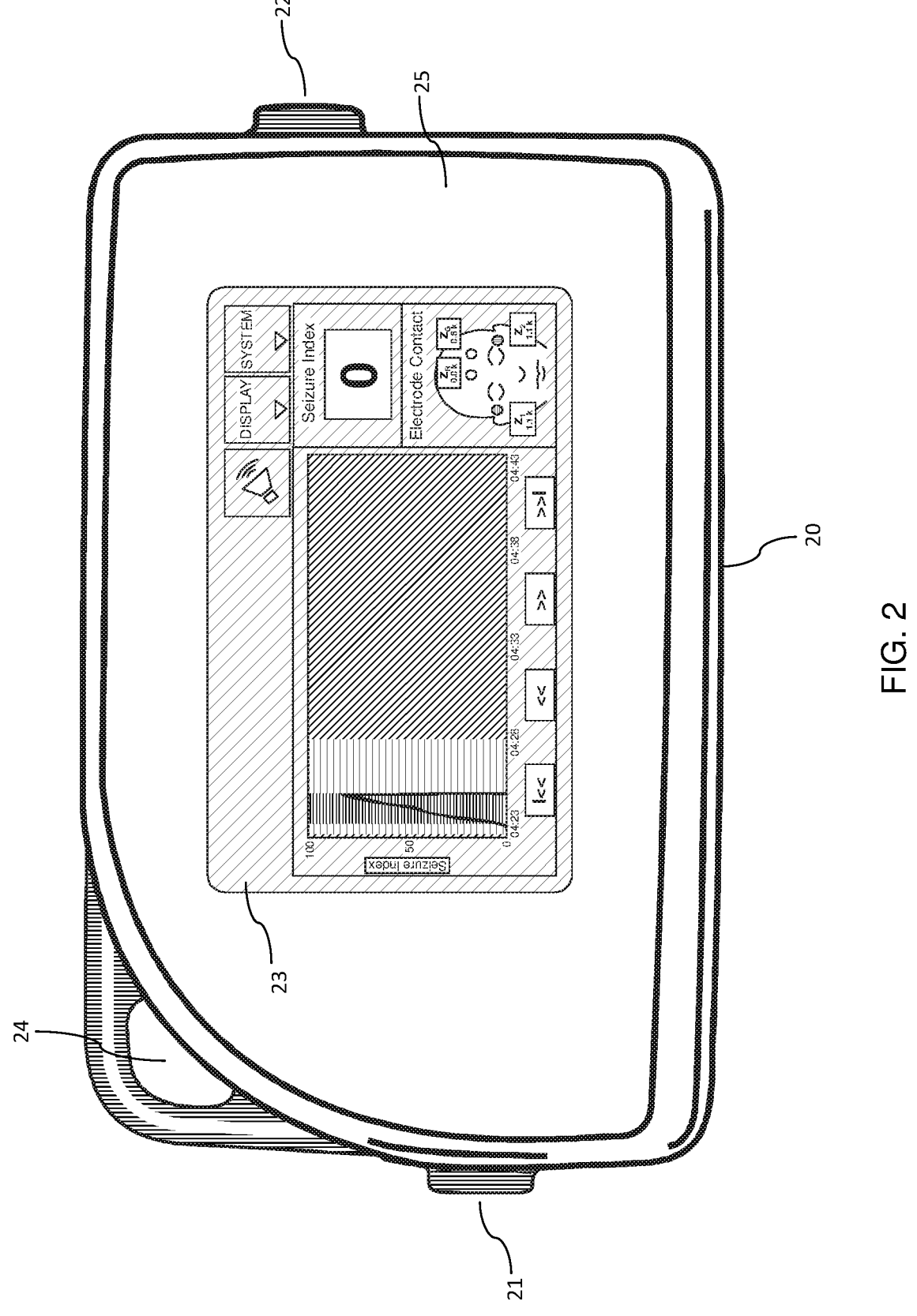
FIG. 2. Schematic of the real-time, automatic, field-deployable and ruggedized brain dysfunction monitor.

FIG. 2 shows a schematic of the real-time, automatic, field-deployable and ruggedized brain dysfunction monitor. The Patient Monitor 20 presents itself under the form of a plastic enclosure 25 housing the electronics (not shown) and the computing and display means 23. The enclosure 25 is designed in such a way that water and dust ingress is minimized. The system has 2 connectors 21, 22. The Power/Data connector 21 provides the means to supply power to the system, recharge the battery, and transfer data. The Patient Cable connector 22 provides the means of attaching a cable containing the electrode leads. This cable can be removed for easy cleaning. In the preferred embodiment, a touch screen display 23 is embedded in the enclosure, and provides users with an interface to display the patient's brain state, and interface with the instrumentation amplifiers.

The enclosure has also the means of securely fastening the system to an intravenous pole and/or stretcher bars. This is done using a locking or spring-loaded clamp at the back of the unit. Another attachment means is provided in the form of an opening 24 in the plastic enclosure 25. This opening is used to hang the system onto a hook.

Figure 3:
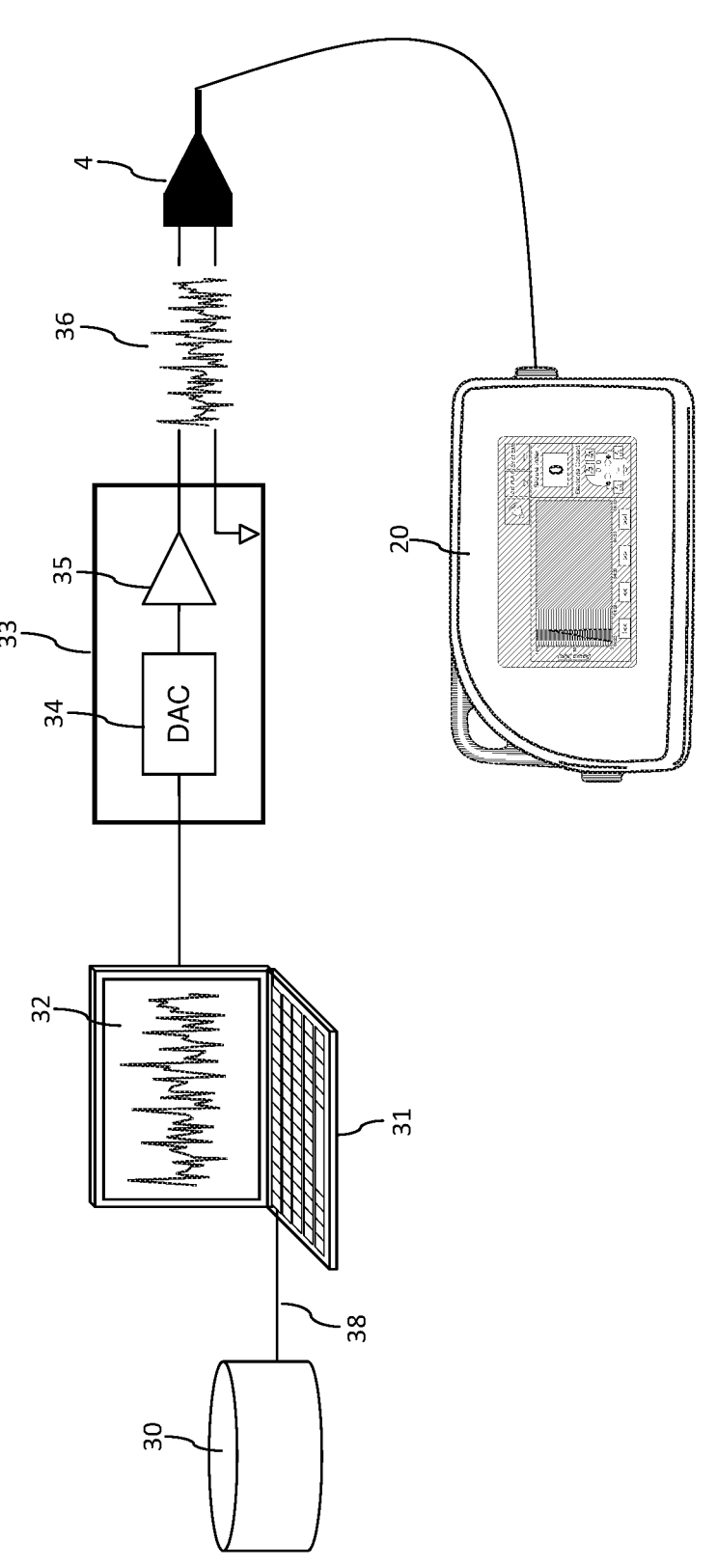
FIG. 3 Schematic of a virtual patient bench test system.

FIG. 3 shows a virtual patient bench test system. A bench test system was designed in order to provide the means for testing the real-time capability of the system. The bench test system makes use of a database of pre-recorded EEG signals contained in a mass storage sub-system 30, which can be accessed wirelessly (not shown), through a network (not shown), or through a serial/parallel data link 38. The pre-recorded signals are accessed by a computer 31, such as a laptop. The data can be displayed on the laptop screen 32 for visual inspection. They are further formatted and sent through a serial/parallel data link to the sub-system 33, further referred to as Virtual Patient (VP). The VP 33 buffers a short segment of the digital EEG data. Once the buffer is full, the VP 33 outputs the digital data to a Digital-to-Analog Converter (DAC) 34, which converts the digital data into an analog equivalent. The digital data are sent to the DAC 34 at a rate consistent with real-time. Once sent to the DAC 34, they are removed from the buffer. Communication means between the computer and the VP ensures that the buffer is always kept full by adding new data from the original database. This communication may be done in real-time or faster.

An attenuator stage 35 reduces the amplitude of the analogue signal 36 in such a way that a micro-volt range is achieved. The gain of the attenuator if specifically designed such that the VP output is an equivalent, both in terms of waveform and amplitude, to the original digital data. Care is taken to reduce the output noise of the VP such that the ECS detection methods and algorithms can be tested (the output noise of the VP superimpose to the analogue EEG equivalent, which may prevent the monitoring system to detect periods of ECS).

Besides for pre-recorded EEG data, the bench test VP can also be used to generate arbitrary waveforms to evaluate the electrical characteristics of the instrumentation amplifiers of the tested system.

Figure 4:
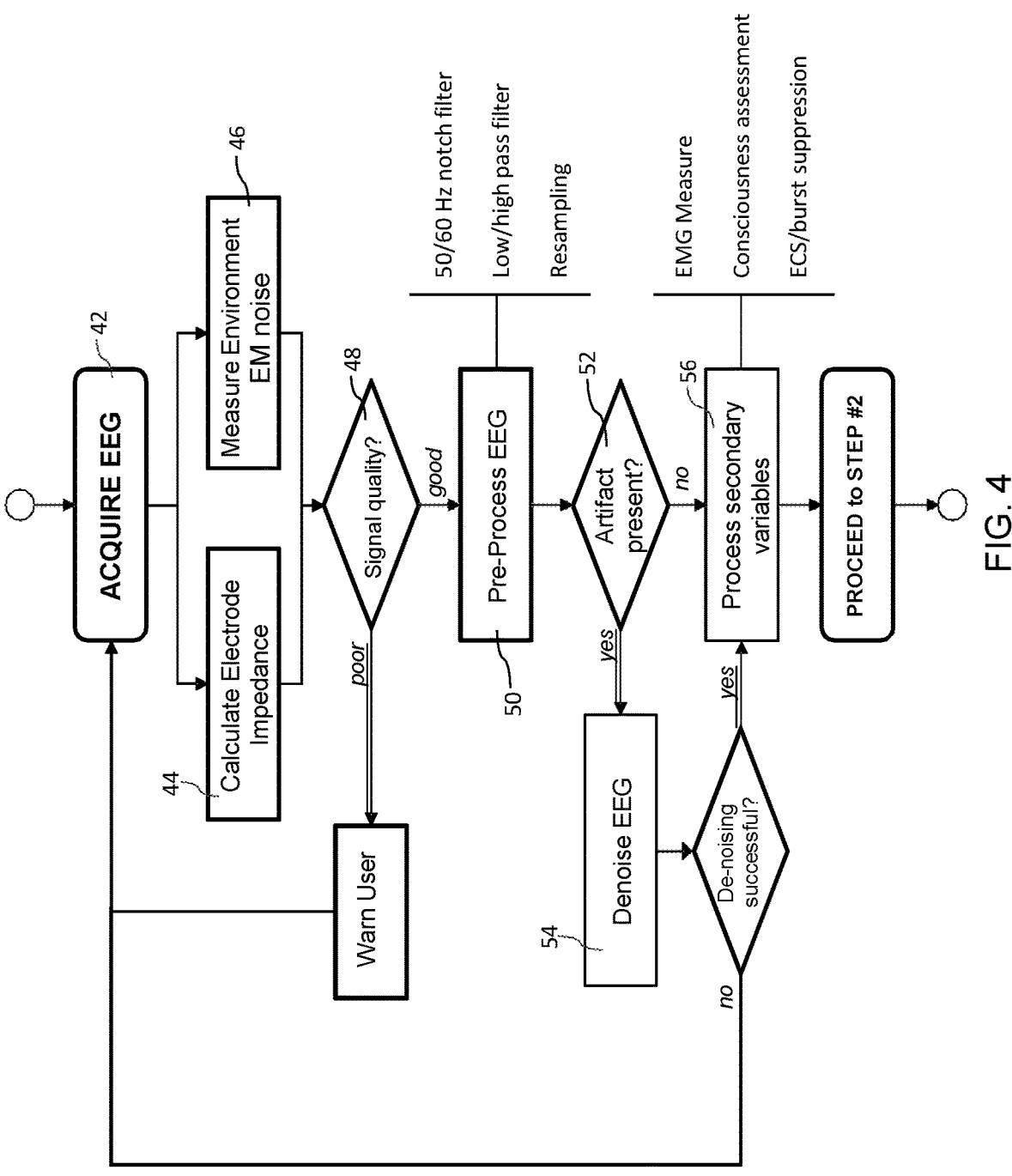
FIG. 4 Flow diagram of the signal acquisition and pre-processing flow chart for one of the many embodiments.

FIG. 4 shows a diagram of the signal acquisition and pre-processing flow for one of the many embodiments. After the acquisition of the current EEG epoch 42, the signal quality is measured by means of continuous impedance 44 and Electro-Magnetic (EM) noise 46 measures. If the signal quality is good 48, the system proceeds by applying a series of pre-processing filters 50. Resampling is carried out at this stage in order to provide the different algorithms with signals that are of the proper rate. Preferably, a sampling rate of 128 S/s is used for most analyses and signal processing methods.

A sampling rate of 256 S/s is used to determine the EMG power. Once pre-processing is done, the algorithm proceeds to determining whether corrupting artifacts are present 52 in the signal. In some cases, corrupting artifacts can be removed from the signal by denoising 54 without affecting the underlying true EEG information needed for the subsequent analyses. In this case, the algorithm proceeds by calculating secondary variables 56 which may offer a complement of information regarding the patient's brain state. In case the corrupting artifacts are too severe to be removed (e.g., they corrupt the whole frequency band), the epoch is dropped out of the analysis.

In the preferred embodiment, the secondary variables are the electromyogram (EMG) activity (power in the 70-110 Hz band), a consciousness index representing the level of consciousness of the patient, and the detection of electrocortical silence (ECS) in order to determine the suppression ratio (percentage of ECS epoch in the last 60 seconds).

Figure 5:
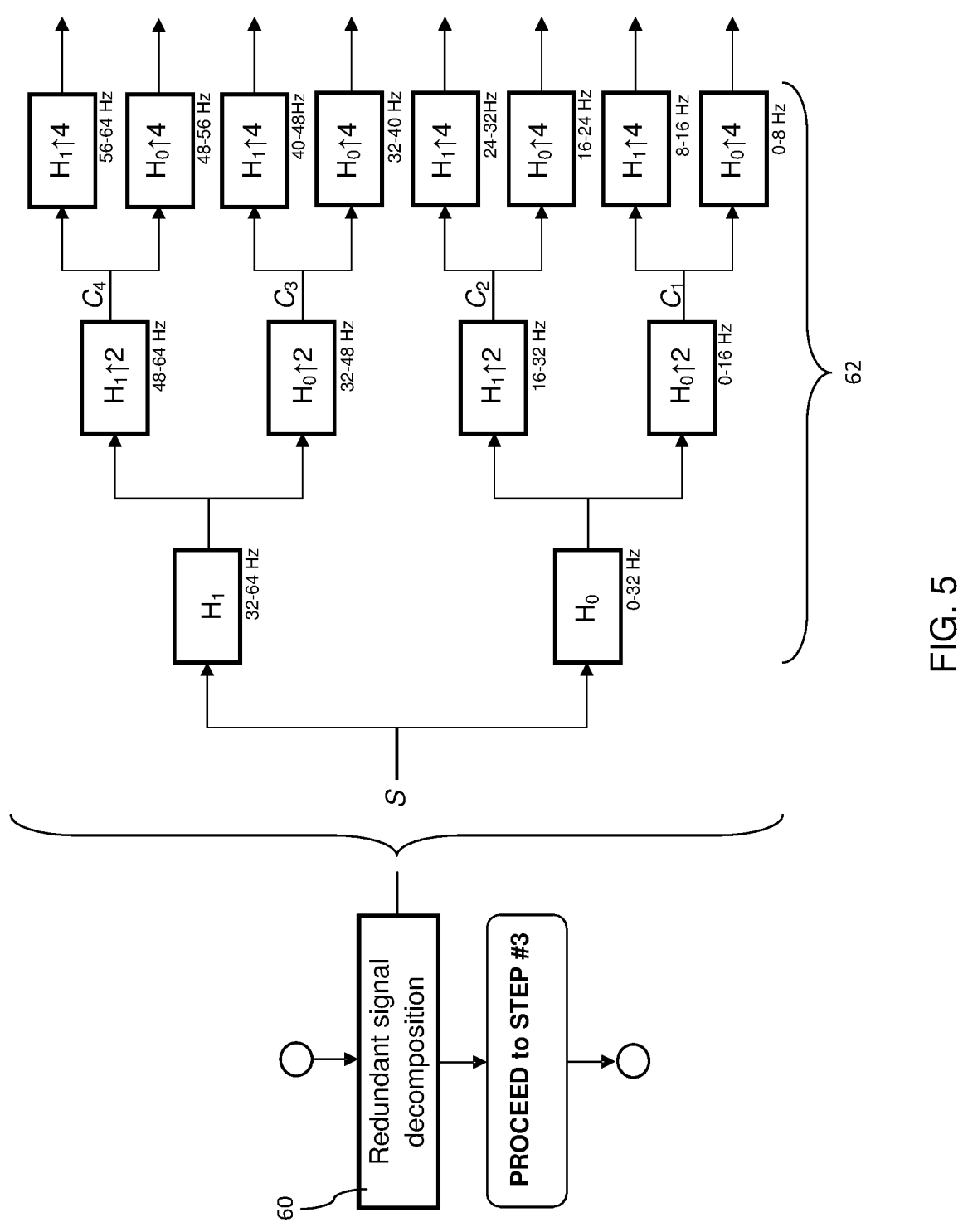
FIG. 5 Flow chart and block diagram of redundant wavelet packet (RWP) decomposition (3-level).

FIG. 5 is a flow chart and block diagram of redundant wavelet packet (RWP) decomposition (3-level). In FIG. 5, the redundant signal decomposition 60 is carried out through three levels of filter banks 62.

Figure 6:
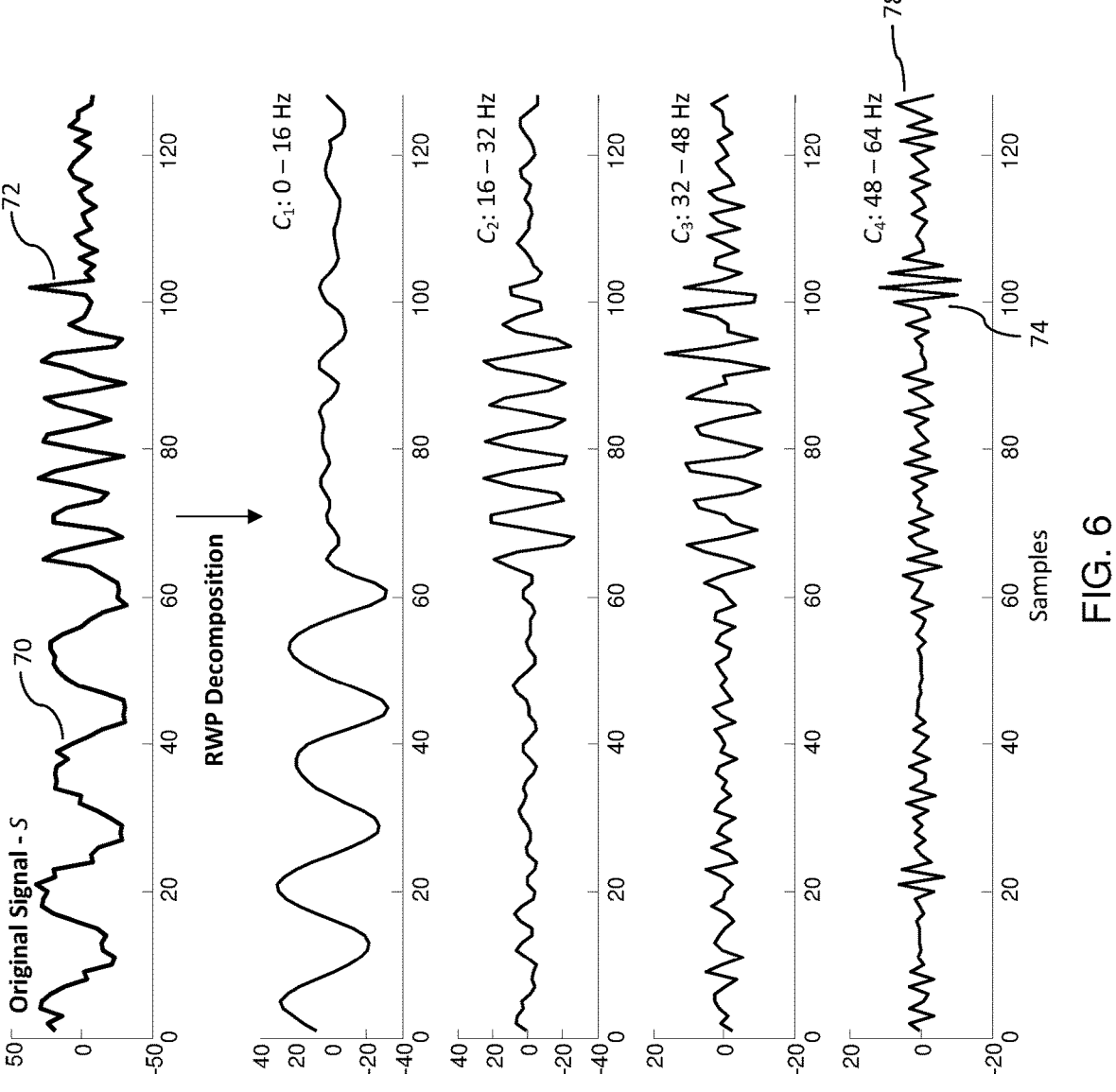
FIG. 6 Examples of a RWP decomposition (2-level).

FIG. 6 are examples of a RWP decomposition (2-level). The original signal S 70 contains random white noise as well as different frequency components, and a single spike 72 at time t=102 samples. It is interesting to see how the redundant decomposition captured well these components in the signal. Even the short transitory spike is evident 74 in the high frequency band 78.

FIG. 7 are examples of synchronization 80 of the RWP coefficients for a single spike 82.

Figure 8:
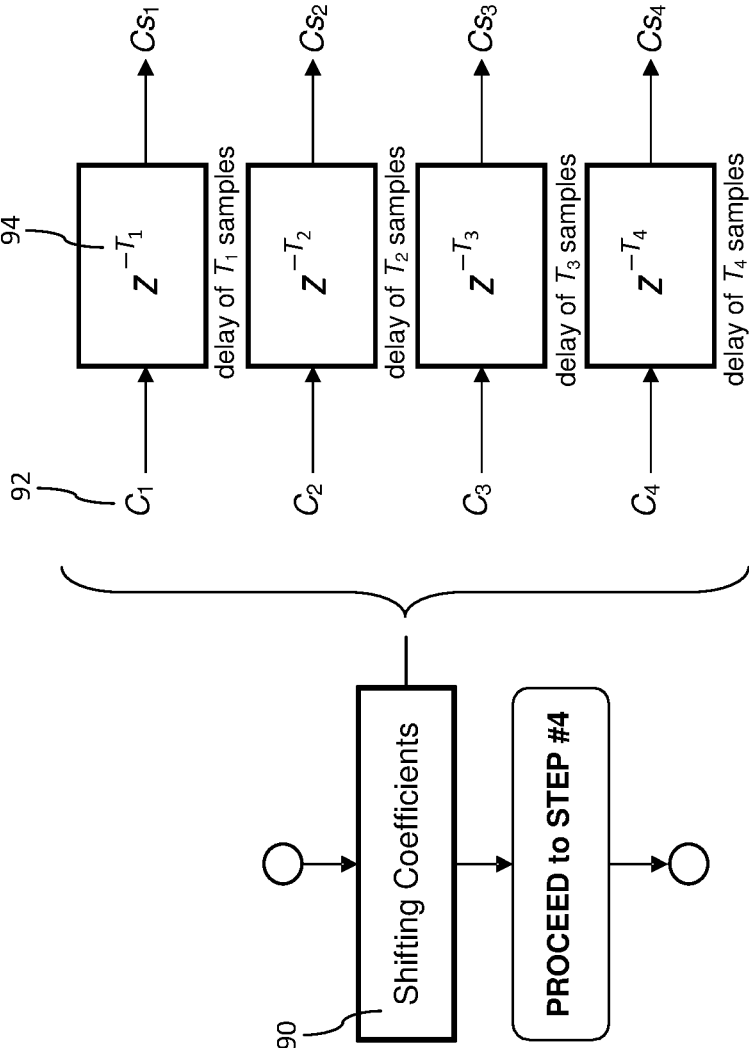
FIG. 8 Example of the synchronization by shifting RWP coefficients in bands of decomposition using appropriate time shift.

FIG. 8 is an example of the synchronization by shifting RWP coefficients 90 in bands 92 of decomposition using appropriate time shifts 94.

Figure 9:
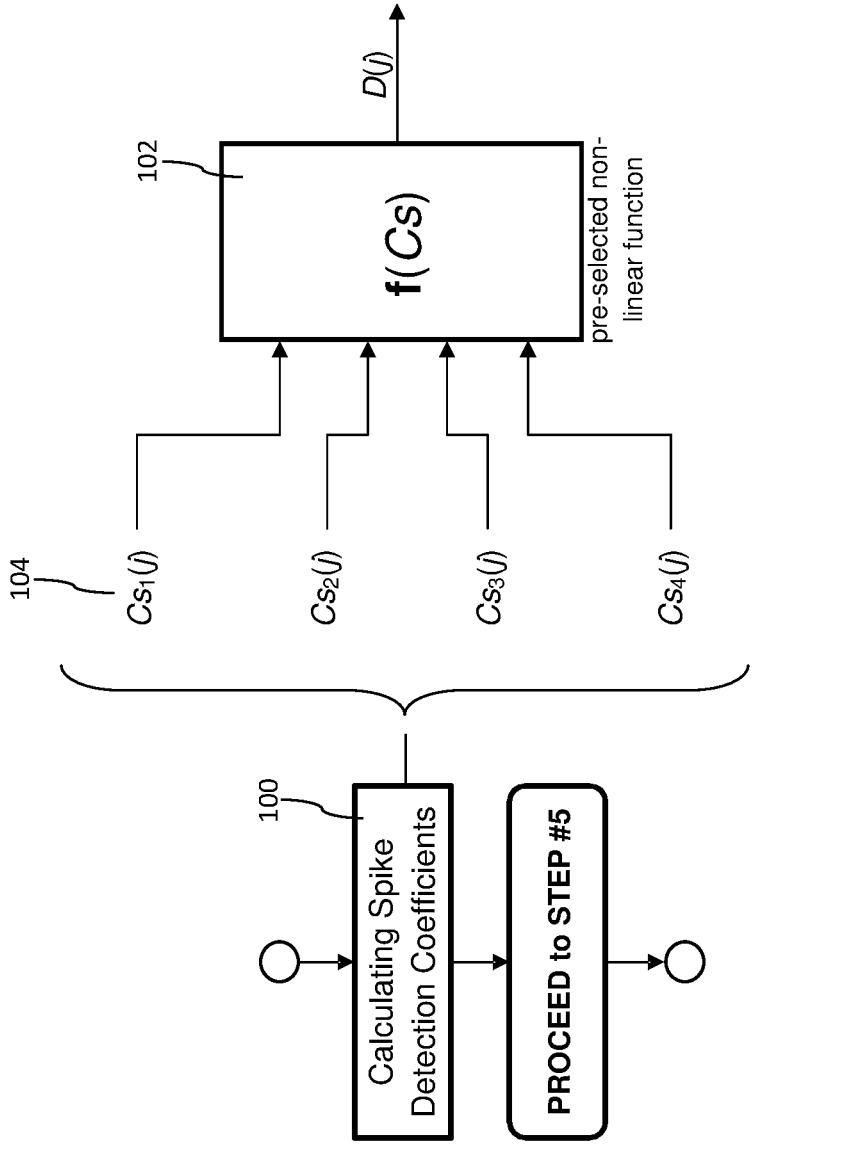
FIG. 9 Example of the calculation of the spike detection coefficients by applying a spike detection function on the shifted RWP coefficients.

FIG. 9 is an example of the calculation of the spike detection coefficients 100 by applying a spike detection function 102 on the shifted RWP coefficients 104.

Figure 10:
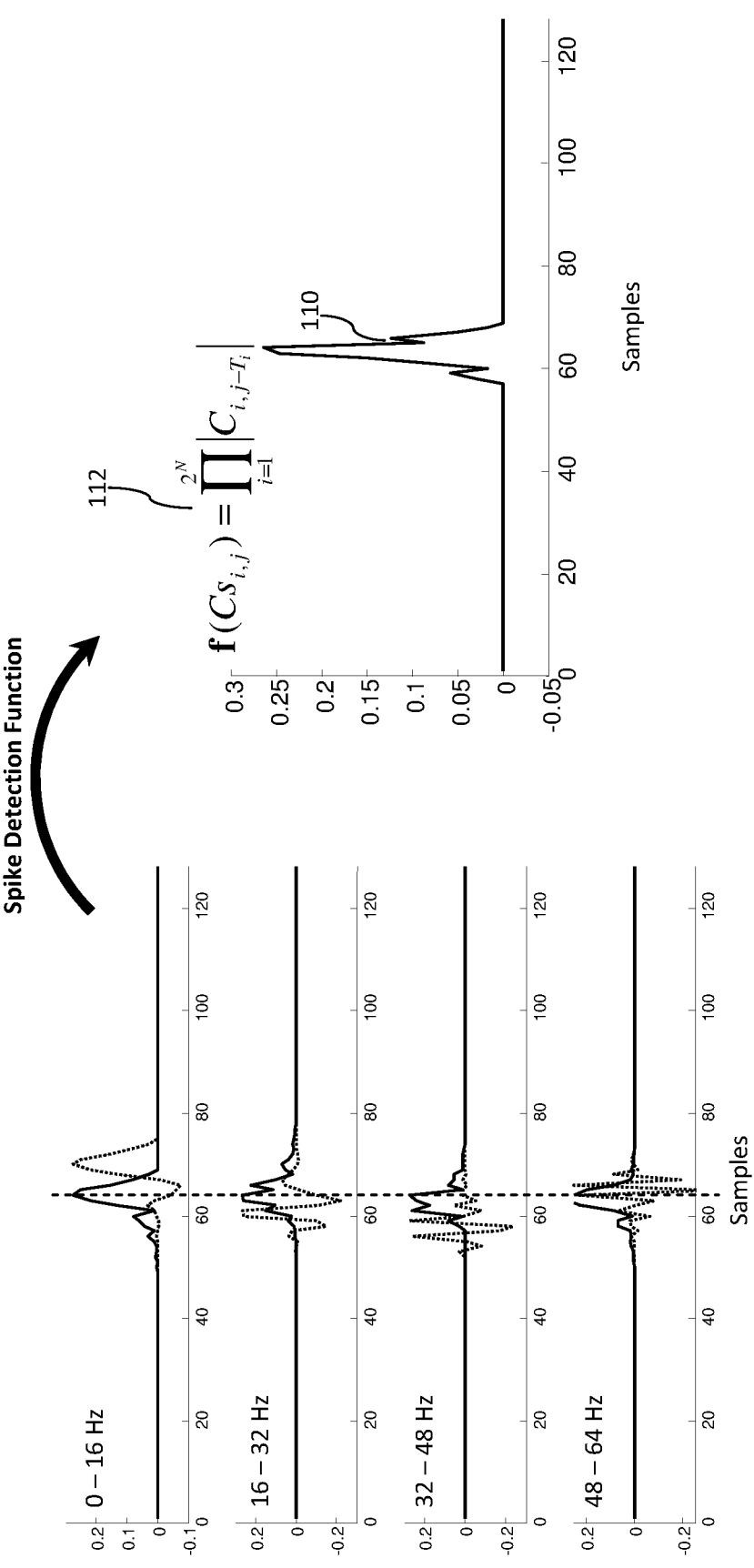
FIG. 10 Examples of spike detection coefficients obtained for the single spike example through the application of a spike detection function.

FIG. 10 are examples of spike detection coefficients 110 obtained for the single spike example (not shown) through the application of a spike detection function 112.

Figure 11:
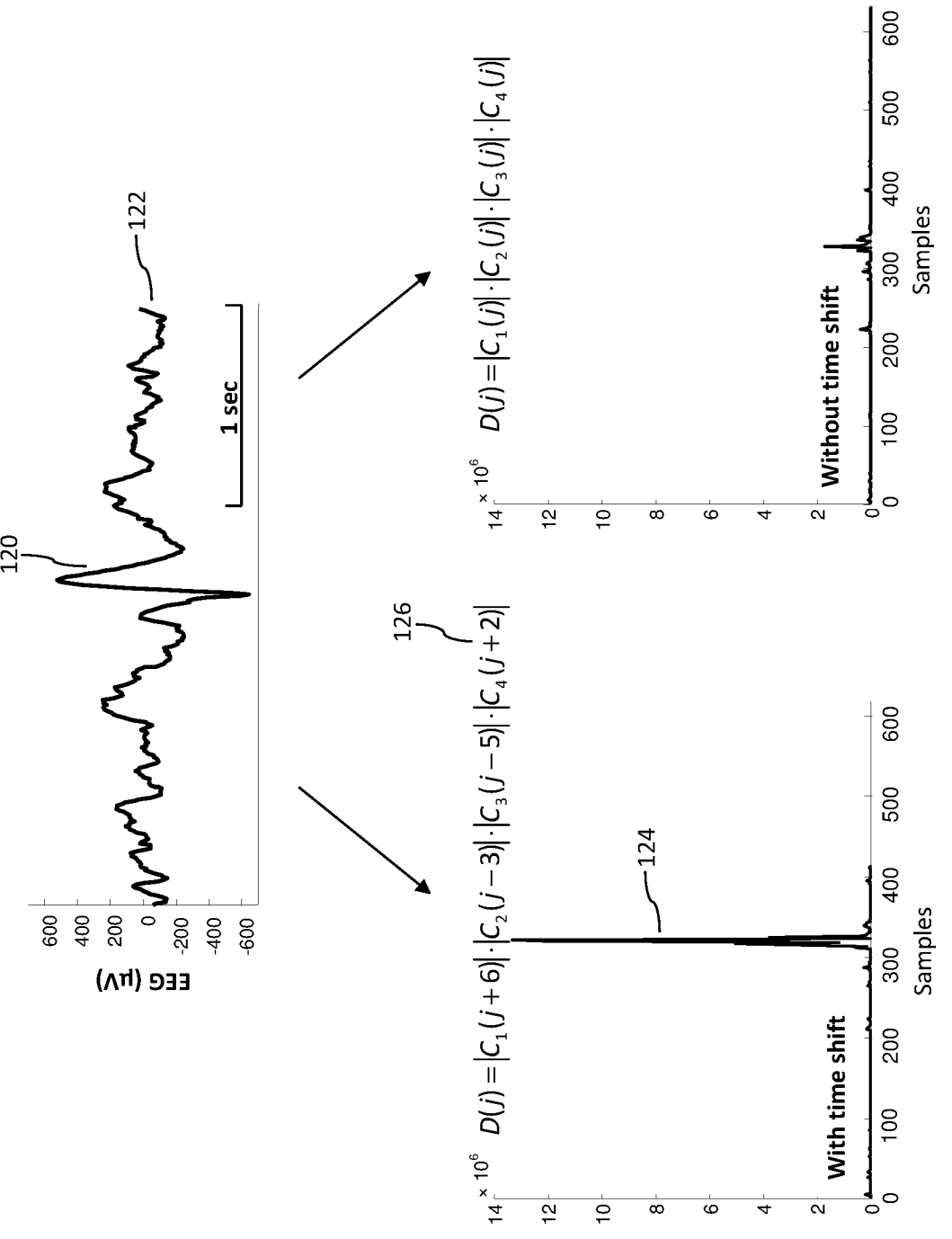
FIG. 11 Examples of an isolated spike in an ECOG recording and its amplification by the spike detection function.

FIG. 11 are examples of an isolated spike 120 in an ECoG recording 122 and its amplification by the spike detection function 126. The amplification effect of the synchronization of the wavelet coefficients is obvious, as it yields more prominent detector coefficients 124 which can be more easily distinguished from normal background EEG activity.

Figure 12:
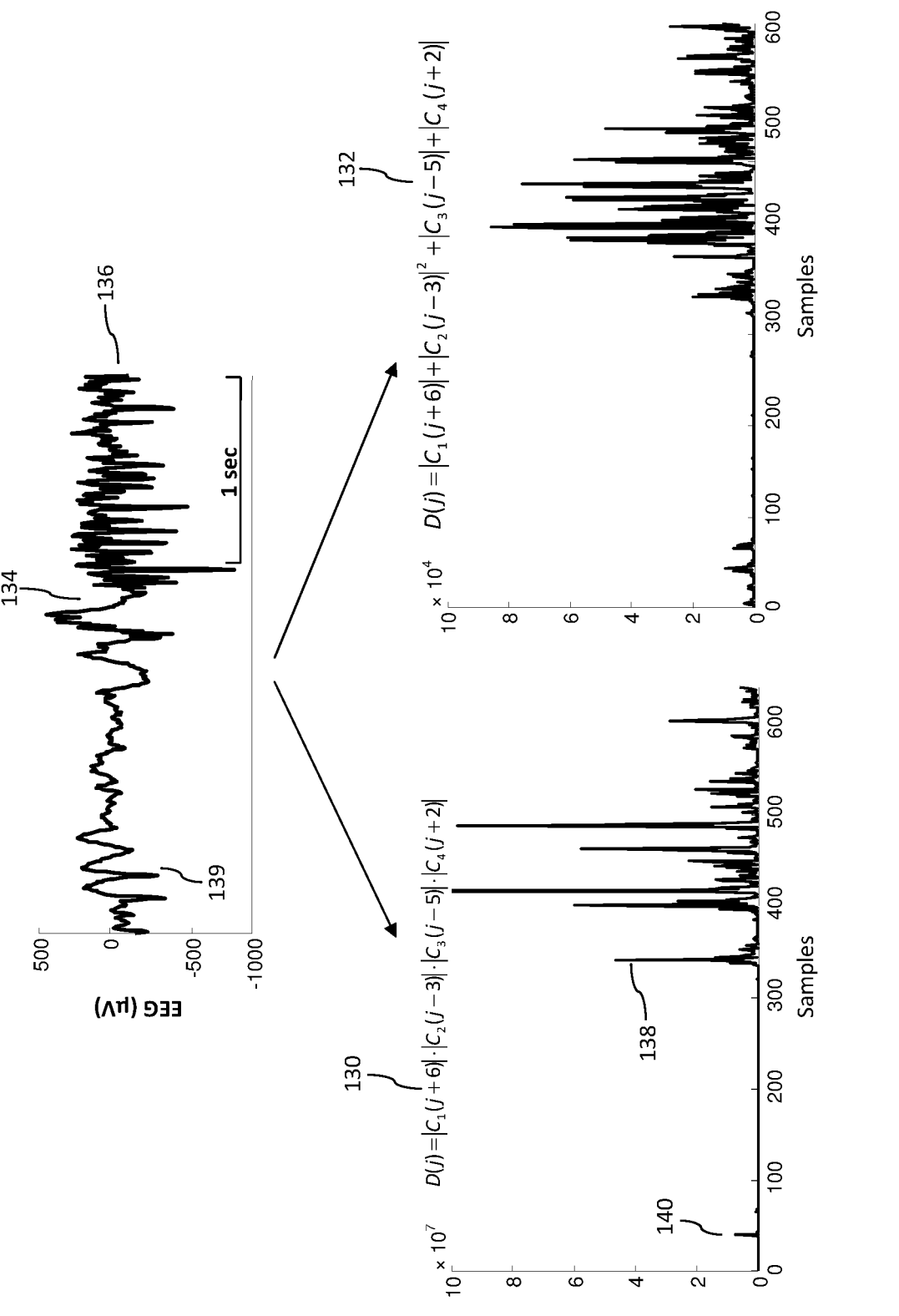
FIG. 12 Examples of two separate/different Spike Detection functions for detection of a seizure onset in an ECoG recording.

FIG. 12 are examples of two separate/different Spike Detection functions 130, 132 for detection of a seizure onset 134 in an ECoG recording 136. The start of the seizure 134 is very well detected 138 even though the initial spikes are buried in the background activity. The first spike detection function yields more prominent coefficients and is better at minimizing 140 the artifact 139 localized at the beginning of the recording. Yet, it is more sensitive to EMG activity and the second function 132 is preferred for scalp EEG analysis.

Figure 13:
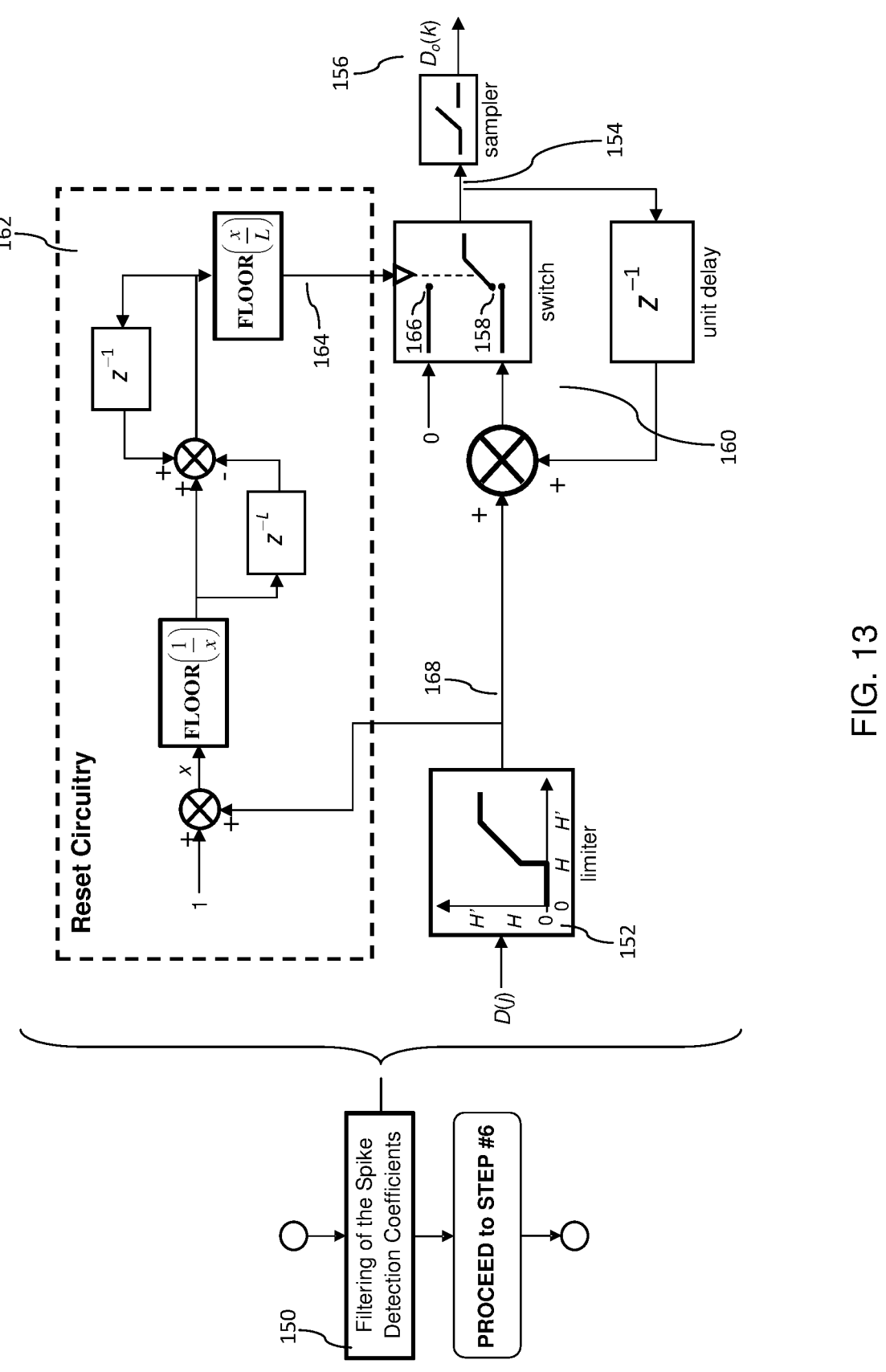
FIG. 13 Block diagram depicting output filtering of the spike detection coefficients.

FIG. 13 is a block diagram depicting output filtering 150 of the spike detection coefficients. Thresholding 152 is coupled with a resettable integrator 154 to yield an un-scaled seizure index 156. The switch 158 in the integrator loop 160 is controlled through a reset circuitry 162. When the output 164 of the reset circuitry 162 is 1, the switch 158 toggles to its high position 166 and outputs 0. The reset circuitry 162 effectively counts the number of thresholded D(j) coefficients 168 that are equal to 0 in the last L samples. If this number is equal to L, the circuitry 162 outputs 1. It outputs 0 otherwise. The output of the filter is a single value which represents the seizure activity of the $k^{th}$ epoch.

Figure 14:
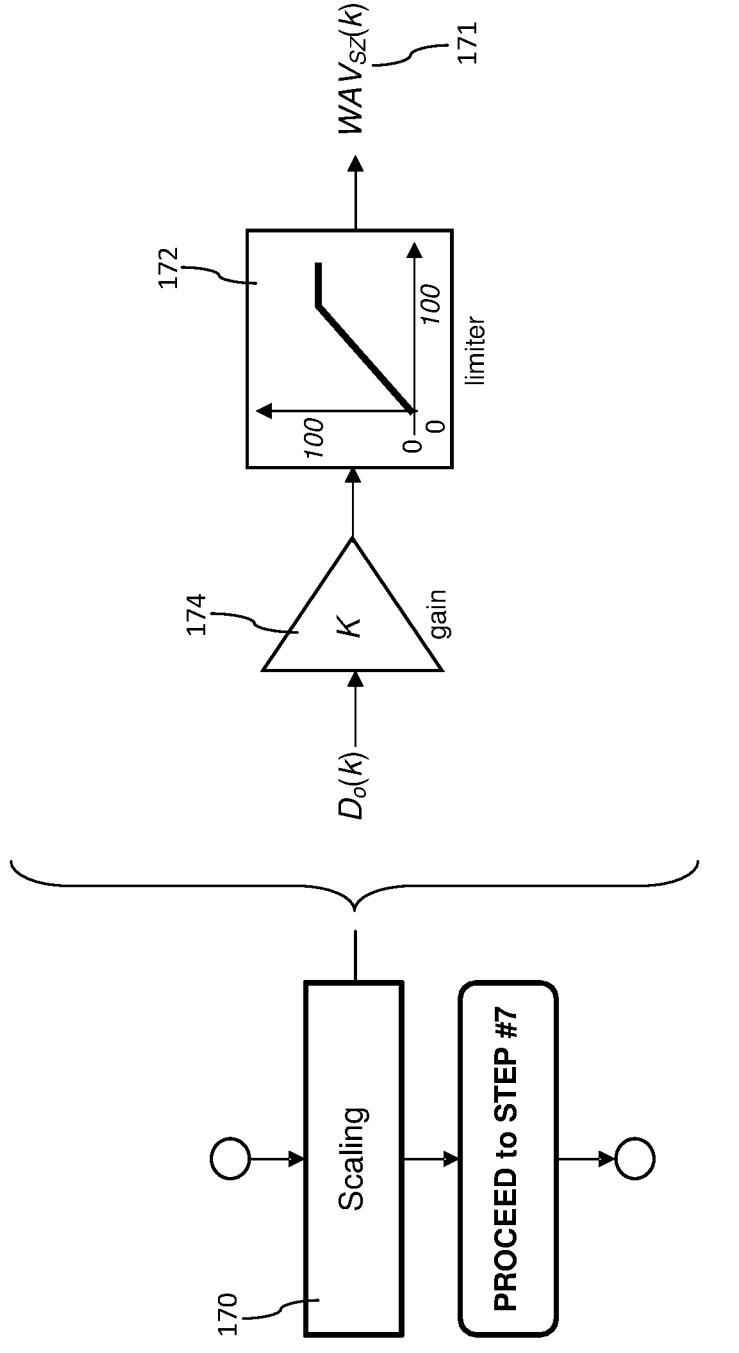
FIG. 14 Block diagram showing scaling of the seizure index.

FIG. 14 is a block diagram showing scaling 170 of the seizure index. In the preferred embodiment, the WAV$_{SZ}$ scale 171 is obtained through a limiter 172 with a scale from 0 to 100, where 0 denotes the absence of any seizure activity, and 100 denotes the presence of strong and sustained seizure activity. In the preferred embodiment, the K factor 174 is $1e^{-9}$.

FIG. 15 is an example of the WAV$_{SZ}$ index 190 for a 5-minute scalp EEG recording 192 containing 2 separate generalized seizures 194, 196. The recording started in the middle of a seizure. The WAV$_{SZ}$ index 190 can be shown to automatically detect the beginnings and the ends of the seizures where it crosses above a threshold H$_s$ 204, represented on the graph by a dashed white line.

Figure 16:
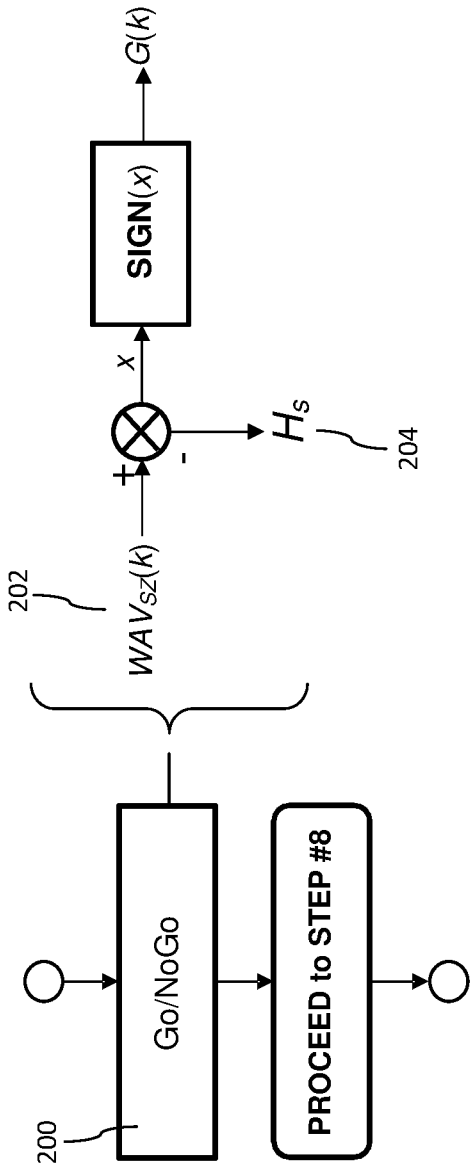
FIG. 16 Block diagram of a seizure detection (Go/NoGo) based on $\text{WAV}_{SZ}$ index and appropriate threshold $H_s$.

FIG. 16 is a block diagram of a seizure detection (Go/NoGo) 200 based on WAV$_{SZ}$ index 202 and appropriate threshold H$_s$ 204.

Figure 17:
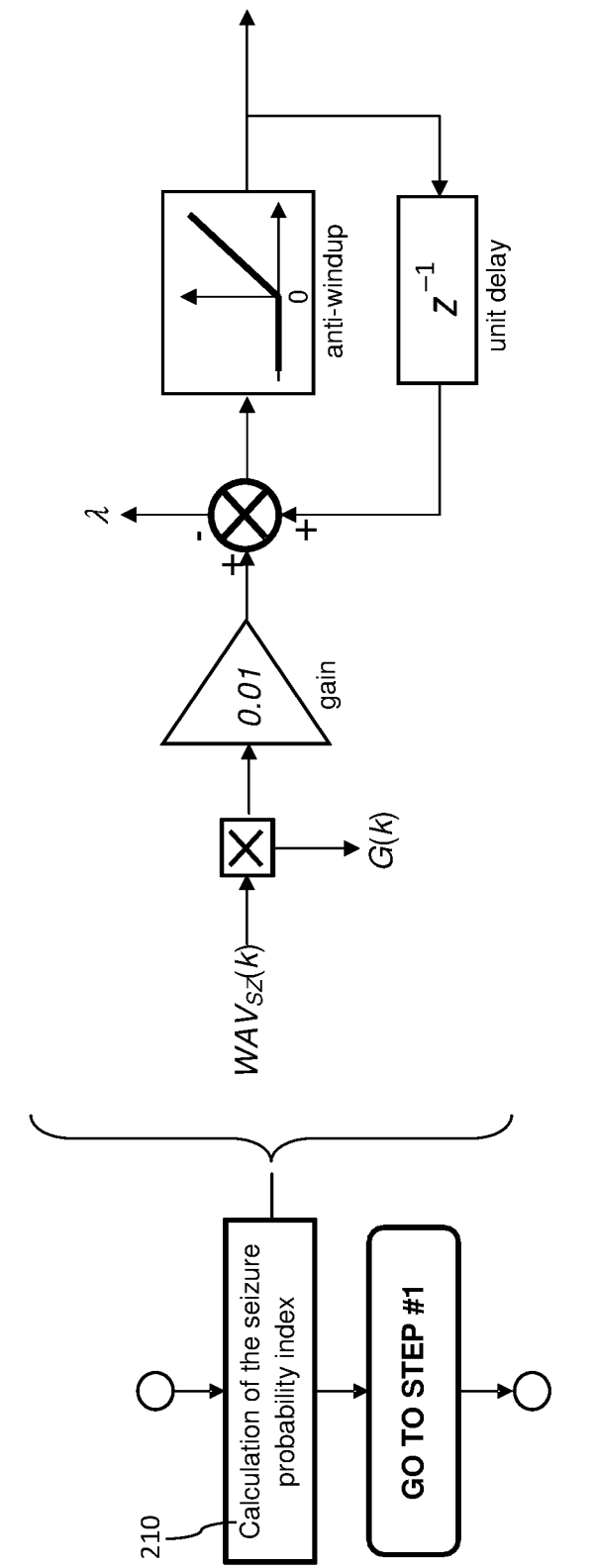
FIG. 17 Block diagram of the calculation of the seizure probability index for diagnostic purposes.

FIG. 17 is a block diagram of the calculation of the seizure probability index 210 for diagnostic purposes.

Figure 18:
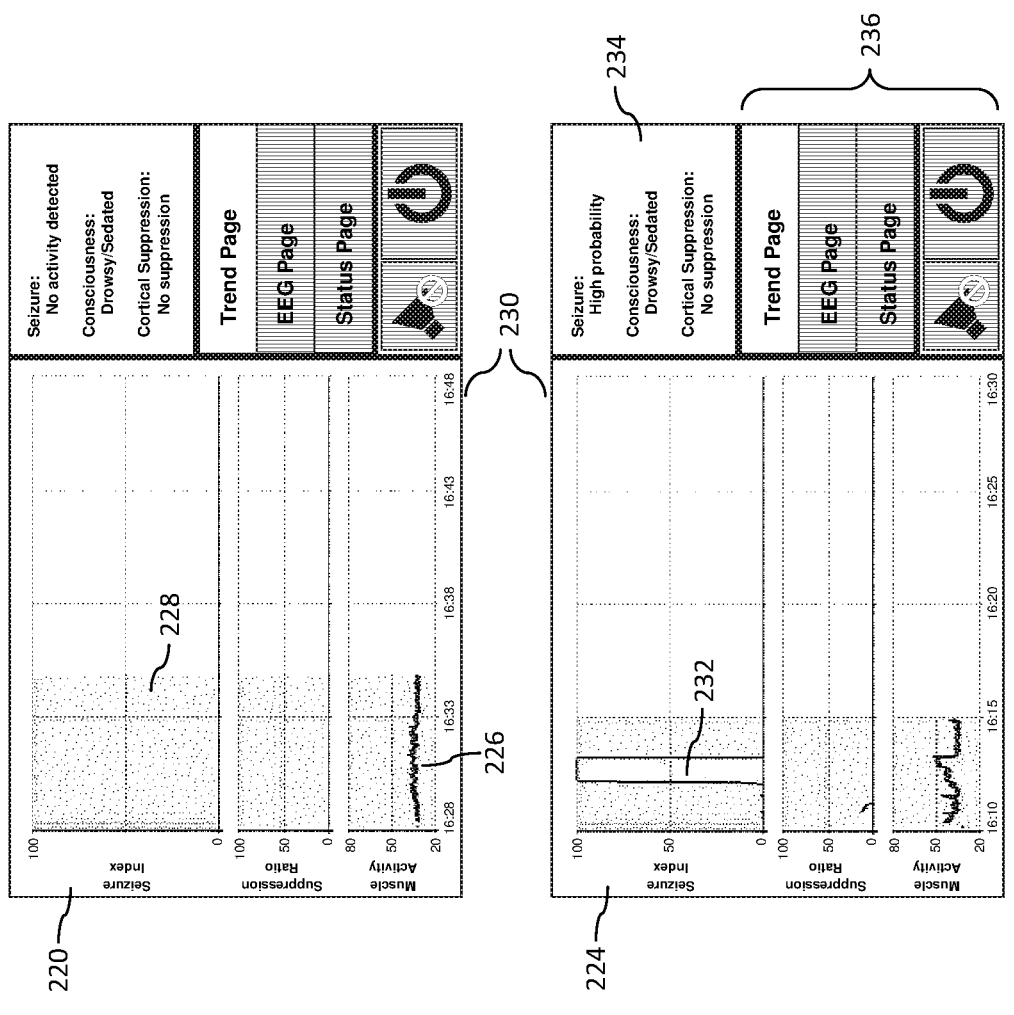
FIG. 18 Picture of the monitor screen for an embodiment of the present invention.

FIG. 18 shows the monitor screen 230 for an embodiment of the present invention under two different conditions. Screen 220 shows a user interface for a_hand-held application. This interface displays the real-time WAV$_{SZ}$ index (which is zero and therefore not shown), a suppression ratio (also zero and therefore not shown), and the EMG activity over a defined amount of time 226. During normal activity, the background 228 of the trends remains green (indicated in the figure by stippling). When seizure activity is detected as shown in similar screen 224, the background shading turns red 232 (indicated in the figure by absence of stippling underneath the seizure index curve), thereby clearly indicating periods of detected seizure activity in the past. In the upper right hand side, text messages 234 provide an interpretation of the different processed variables that are displayed to the user. User controls are provided in the lower right hand side corner 236. Note that the interface in the preferred embodiment is designed for a small touch screen.

Figure 19:
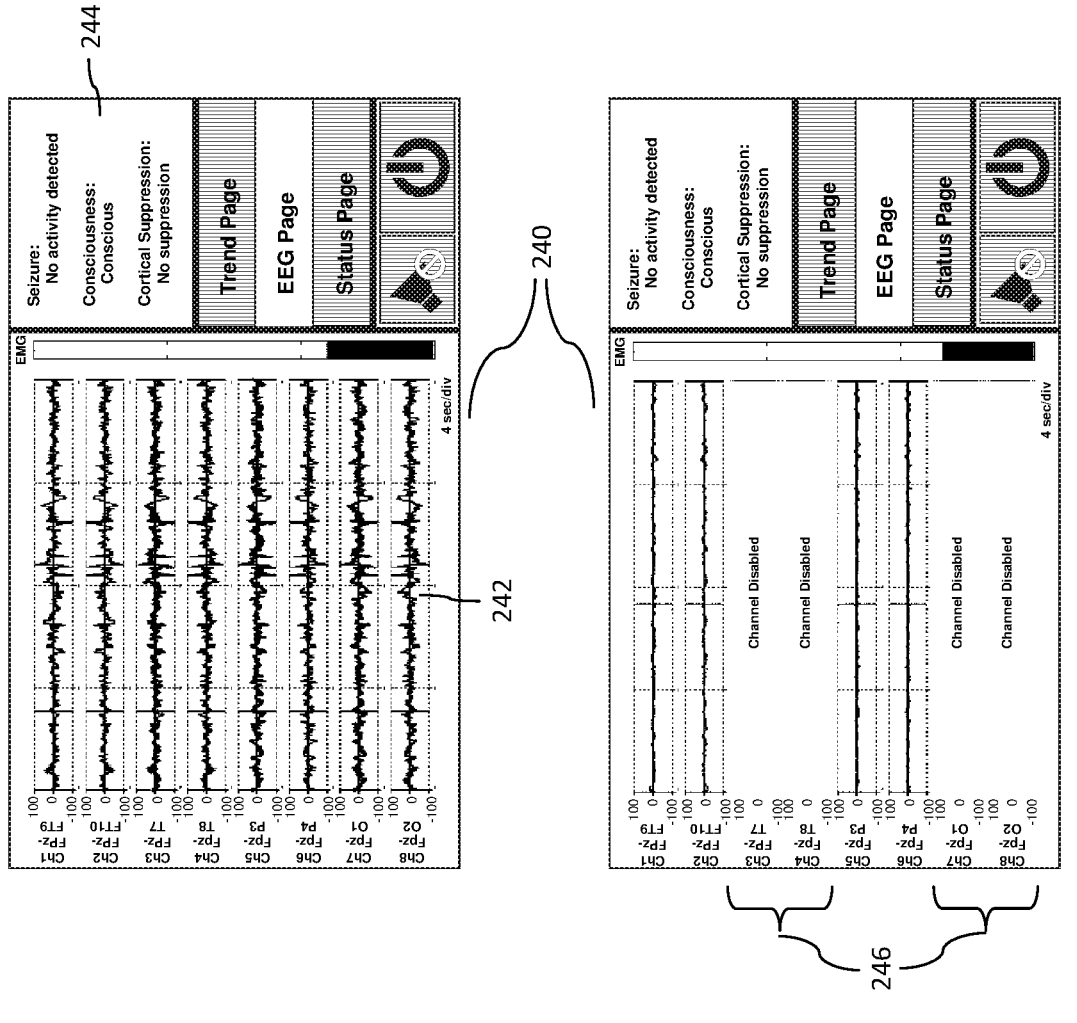
FIG. 19 Picture of the monitor screen for another embodiment of a user interface for hand-held application.

FIG. 19 is a picture of the monitor screen 240 for an embodiment of a user interface for hand-held application. This interface displays the real-time EEG waveforms 242 for easy visual inspection. The diagnostic text messages 244 are kept in the upper right hand-side corner. Channels with poor electrode impedance or disconnected leads are automatically removed 246 from the subsequent analyses. While no analysis is being performed, the system keeps on continuously monitoring these channels in order to detect an eventual improvement in the signal quality. At this point, the channels are automatically enabled are re-incorporated in the analysis scheme. It is important to notice that the analysis methods are automatically adapted depending on the availability of EEG channels.

Figure 20:
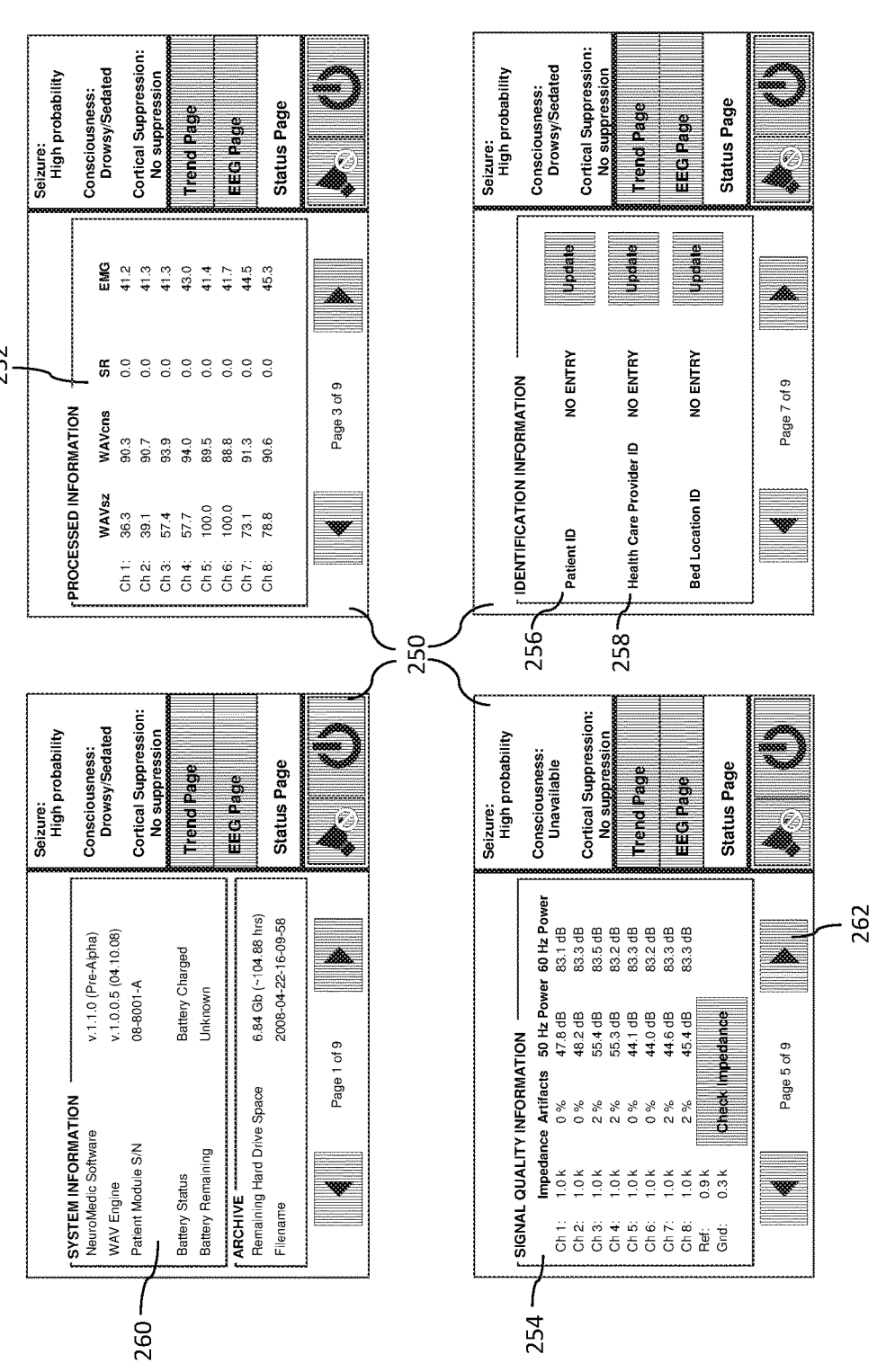
FIG. 20 Picture of the monitor screen for still another embodiment of a user interface for hand-held application.

FIG. 20 illustrates monitor screens 250 for an embodiment of a user interface for hand-held application. These status pages can be used to display various information that may be useful to more advanced users. In particular, the interface can display in real-time all, or a subset of, the processed variables 252, including, per cannel, seizure, consciousness, suppression ratio, and EMG variables. This can include variables calculated to determine the patient's brain state, as well as variables calculated to determine signal quality 254. In addition, identification information pertaining to the patient 256 and the attending user 258 can be added and displayed. Finally, information related to the system itself (calibration values, serial number, software version, remaining battery life and disk space, etc.) 260 can also be displayed. The information presented in the Status Page can span many different pages which can be accessed through Forward/Backward buttons 262.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

The invention claimed is:

1. A system for detecting seizures or brain dysfunction comprising:
 at least two electrodes each configured to receive a signal from a patient's brain wave activity;
 a patient module comprising at least one processor configured with an algorithm, the at least one processor configured to input the signals from the at least two electrodes, the algorithm, when executed by the at least one processor causes the at least one processor to apply a transform to the signals to obtain at least two coefficients from the signals, align and combine the coefficients corresponding with at least one abnormal pattern signal, identify a seizure or brain dysfunction from the signals of the patient by comparing aligned then combined coefficients corresponding to the at least one abnormal pattern signal to a threshold, and an output signal based on the identified seizures or brain dysfunction; and
 an output device configured to treat the seizure or the brain dysfunction by administering a physical, electrical or chemical treatment based, in part, on the output signal.

2. The system in claim 1, further comprising at least two leads for each of the at least two electrodes, the leads for inputting the signals from the at least two electrodes, the leads or a harness incorporating the leads being shielded from cardiac defibrillation or like voltages.

3. The system in claim 1, wherein the patient module further comprises a circuit breaker for shielding the patient module from cardiac defibrillation or like voltages.

4. The system in claim 1, wherein the patient module is further capable of performing a continuous impedance check on the at least two electrodes.

5. The system in claim 1, wherein the system is portable and weighs less than 2 lbs.

6. The system in claim 1, wherein the patient module further comprises at least two input channels and the input channels are automatically calibrated by the at least one processor of the patient module.

7. The system in claim 1, wherein the at least two electrodes are brain-contacting electrodes and the output device is configured to treat seizure or brain dysfunction by administering the electrical treatment through the brain electrodes.

8. The system in claim 1, wherein the output signal is output to the output device for treatment purposes in real-time.

9. The system in claim 7, wherein the patient module is configured to be positioned within a body of the patient or external thereto.

10. The system in claim 7, wherein the brain electrodes are implantable brain electrodes.

11. The system in claim 1, wherein the at least two electrodes have leads and the leads are shielded to protect the patient module from electromagnetic interference and electrostatic discharge.

12. The system in claim 7, wherein the at least two electrodes have leads and the leads are shielded to protect the patient module from electromagnetic interference and electrostatic discharge.

13. The system in claim 1, wherein the algorithm executed by at least one processor further causes the at least one processor to create an index which is represented by a numerical value corresponding to the level of abnormal pattern signal, and where the index is compared against the threshold to determine whether seizure activity is occurring in the patient in real-time.

14. The system in claim 7, wherein the algorithm executed by the processor further causes the processor to create an index which is represented by a numerical value corresponding to the level of abnormal pattern signal, and where the index is compared against the threshold to determine whether seizure activity is occurring in the patient in real-time.

15. The system of claim 1, wherein the patient module is configured to transmit raw and/or analyzed data to a computer or cellular phone for display, and/or to notify a care provider of a present or recent neurophysiological status of the patient.

16. The system of claim 7, wherein the patient module is configured to transmit raw and/or analyzed data to a computer or cellular phone for display, and/or to notify a care provider of a present or recent neurophysiological status of the patient.

17. The system of claim 1, wherein the patient module is configured to transmit raw and/or analyzed data to remote locations for data storage and/or review.

18. The system of claim 1, wherein the patient module is configured to transmit raw and/or analyzed data to remote locations for data storage and/or review.

* * * * *